United States Patent [19]
Capet et al.

[11] Patent Number: 5,563,136
[45] Date of Patent: Oct. 8, 1996

[54] 3-UREIDOBENZODIAZEPINONES USEFUL AS ANTAGONISTS OF CCK OR OF GASTRIN

[75] Inventors: Marc Capet, Thiais; Claude Cotrel, Paris; Marie-Christine Dubroeuco, Enghien les Bains; Claude Guyon, Saint Maur des Fosses; Jean-Paul Martin, Colombes, all of France

[73] Assignee: Rhone-Poulenc Rorer S.A., Antony, France

[21] Appl. No.: 211,323

[22] PCT Filed: Oct. 8, 1992

[86] PCT No.: PCT/FR92/00935

§ 371 Date: Apr. 6, 1994

§ 102(e) Date: Apr. 6, 1994

[87] PCT Pub. No.: WO93/07130

PCT Pub. Date: Apr. 15, 1993

[30] Foreign Application Priority Data

Oct. 10, 1991 [FR] France .................... 91 12481

[51] Int. Cl.⁶ .................... A61K 31/55; C07D 243/24
[52] U.S. Cl. .................... 514/221; 540/509
[58] Field of Search .................... 540/509; 514/221

[56] References Cited

FOREIGN PATENT DOCUMENTS

| 434360 | 6/1991 | European Pat. Off. | 540/509 |
|---|---|---|---|
| 434364 | 6/1991 | European Pat. Off. | 540/509 |
| 434369 | 6/1991 | European Pat. Off. | 540/509 |
| 508796 | 10/1992 | European Pat. Off. | 540/509 |
| 508797 | 10/1992 | European Pat. Off. | 540/509 |

*Primary Examiner*—Robert T. Bond
*Attorney, Agent, or Firm*—Finnegan, Henderson, Farabow, Garrett & Dunner, L.L.P.

[57] ABSTRACT

This invention relates to compounds having formula (I),

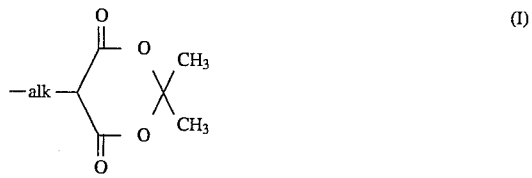

wherein $R_1$ is a hydrogen or halogen atom or an alkyl, alkoxy, alkylthio, nitro, hydroxy or cyano radical; $R_2$ is an alkyl radical or a chain $-CH(R_5)-CO-R_6$; $R_3$ is (a) a phenyl radical substituted by one or a plurality of substituents selected amongst the radicals -alk-$SO_3H$, -alk-$PO_3H_2$, $-CH=NOH$, $-CH-NO$-alk-COOX, $-S$-alk-COOX, $-SO$-alk-COOX, $-SO_2$-alk-COOX, $-CH=CH-$COOX, -alk-CO$-$NHOH, $-C(=NOH)-$COOX, -alk-N(OH)$-$CO-alk, -alk-$SO_2H$, $-CH=CH-SO_3H$, $-C(COOX)=N$-O-alk-COOX, tetrazolyalkyle or a group having a formula (I) or (b) a ring having the formula (A)

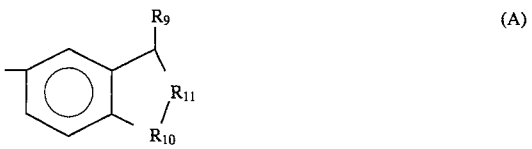

wherein $R_9$ is a radical $=NOX$, $=NO$-alk-COOX, $=CH-$COOX, -alk-COOX, -alk-$SO_2H$ or -alk-$S)_3H$, $R_{10}$ is an oxygen or sulfur atom or a methylene or alkylimino radical and $R_{11}$ is a methylene or ethylene radical, $R_4$ is a pyridyle or phenyl radical optionally substituted by one or a plurality of substituents selected amongst halogen atoms or the alkyl, alkoxy, hydroxy, carboxy, nitro and $-CO-NR_6$ radicals, alk is an alkyl or alkylene radical and X is a hydrogen atom or an alkyl radical. The invention also discloses the salts thereof, their preparation and medicaments containing them.

6 Claims, No Drawings

3-UREIDOBENZODIAZEPINONES USEFUL AS ANTAGONISTS OF CCK OR OF GASTRIN

DESCRIPTION OF THE INVENTION

The present invention relates to derivatives of formula:

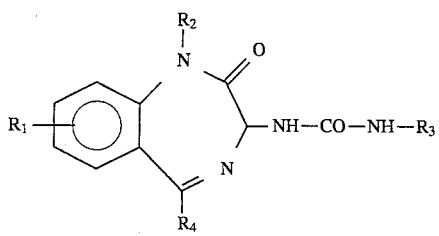

their salts, their preparation and medicaments containing them.

In the formula (I)

$R_1$ represents a hydrogen or halogen atom or an alkyl, alkoxy, alkylthio, nitro, hydroxyl or cyano radical, $R_2$ represents an alkyl radical or a —CH($R_5$)—CO—$R_6$ chain in which $R_5$ represents a hydrogen atom or an alkyl, alkoxycarbonyl or phenyl radical which is optionally substituted (by one or more substituents chosen from amongst halogen atoms and alkyl, alkoxy, alkylthio and nitro radicals) and $R_6$ represents an alkoxy radical, a cycloalkoxy radical which is optionally substituted (by at least one alkyl radical), a cycloalkylalkoxy, phenylalkoxy, polyfluoroalkoxy or cinnamyloxy radical or an —$NR_7R_8$ radical in which $R_7$ and $R_8$, which are identical or different, represent a hydrogen atom or an alkyl radical, a phenyl radical which is optionally substituted (by one or more substituents chosen from amongst halogen atoms and alkyl, alkoxy and alkylthio radicals), or a cycloalkylalkyl, cycloalkyl, indanyl or phenylalkyl radical or else $R_7$ and $R_8$, together with the nitrogen atom to which they are attached, form a saturated or unsaturated monocyclic or polycyclic heterocycle containing 4 to 9 carbon atoms and one or more hetero atoms (O, S, N) and optionally substituted by one or more alkyl, alkoxy, alkoxycarbonyl, dialkylcarbamoyl or phenyl radicals or by spiromonocyclic cyclic system formed by combination of an atom of the heterocycle with 4 to 5 other carbon atoms, one or more of the latter optionally being replaced by hetero atoms (O, S, N), $R_3$ represents (a) a phenyl radical substituted by one or more substituents chosen from amongst -alk-$SO_3H$, -alk-$PO_3H_2$, —CH=NOH, —CH=NO-alk-COOX, —S-alk-COOX, -SO-alk-COOX, —$SO_2$-alk-COOX, —CH=CH—COOX, -alk-CO—NHOH, —C(=NOH)—COOX, -alk-N(OH)—CO-alk, -alk-$SO_2H$, —CH=CH—$SO_3H$, —C(COOX)=N—O-alk-COOX and tetrazolylalkyl radicals or a group of formula:

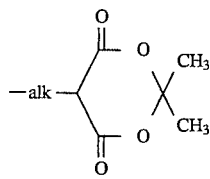

or (b) a cyclic system of formula:

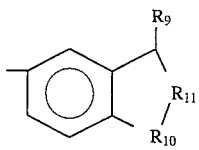

in which $R_9$ represents an =NOX, =NO-alk-COOX, =CH—COOX, -alk-COOX, -alk-$SO_2H$ or -alk-$SO_3H$ radical, $R_{10}$ represents an oxygen or sulphur atom or a methylene or alkylimino radical and $R_{11}$ represents a methylene or ethylene radical, $R_4$ represents a pyridyl or phenyl radical which is optionally substituted by one or more substituents chosen from amongst halogen atoms and alkyl, alkoxy, hydroxyl, carboxyl, nitro and —CO—$NR_6$ radicals, alk represents an alkyl or alkylene radical, X represents a hydrogen atom or an alkyl radical.

In the above definitions and those which will be mentioned below, unless stated otherwise the alkyl, alkylene and alkoxy radicals and the alkyl, alkylene and alkoxy portions contain 1 to 4 carbon atoms in a straight or branched chain, and the cycloalkyl radicals and portions contain 3 to 12 carbon atoms.

When $R_7$ and $R_8$, together with the nitrogen atom to which they are attached, form a heterocycle, the latter is preferably a piperidino, 1-perhydroazepinyl, 1,2,3,6-tetrahydro-1-pyridyl, 1,2,3,4-tetrahydro-1-quinolyl, 1-pyrrolidinyl, 1,2,3,4-tetrahydro-2-isoquinolyl, morpholino, thiomorpholino or 1-indolyl cyclic system, it being possible for these cyclic systems to be optionally substituted by one or more alkyl radicals.

The compounds of formula (I) comprise one or more asymmetric centers which give isomeric forms. The racemates and the enantiomers of these compounds are likewise a part of the invention.

The compounds of formula (I) can be prepared by reaction of a reactive derivative of carbamic acid, optionally obtained in situ by the action of a reactive derivative of carbonic acid chosen from amongst N,N'carbonyldiimidazole, phosgene, trichloromethyl chloroformate, bis(trichloromethyl) carbonate and p-nitrophenyl chloroformate on a derivative of formula:

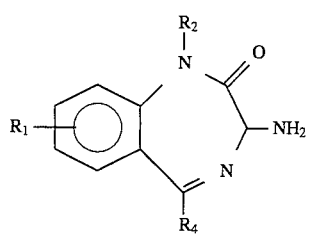

in which $R_1$, $R_2$ and $R_4$ have the same meanings as in the formula (I), with a derivative of formula:

$$H_2N—R_3 \quad (III)$$

in which $R_3$ has the same meanings as in the formula (I) or, when $R_3$ comprises a COOH, $PO_3H_2$, $SO_2H$ or $SO_3H$ radical, a salt of such a compound.

This reaction is preferably carried out in an inert solvent such as tetrahydrofuran, dimethylformamide, a chlorinated solvent (chloroform or 1,2-dichloroethane, for example) or an aromatic solvent (benzene or toluene, for example), at a temperature of between 20° C. and the boiling point of the solvent. The salts used are preferably a salt with an alkali metal (sodium or potassium, for example) or a tetraalkylammonium salt (tetrabutylammonium, for example).

The derivatives of formula (II) can be obtained by application or adaptation of the methods described in the U.S. Pat. Nos. 3,371,084, 3,652,634, the patent applications DE 3,907,390, NL 327,674, EP 349,949 and EP 385,735, by I. FRYER, Bicyclic diazepines, diazepine with an additionnal ring, John Wiley & Sons Inc., M.G. BOCK et al., J. Org. Chem., 52, 3232 (1987) and in the examples.

The derivatives of formula (III) are commercially available or can be obtained by application or adaptation of the methods described by R. SCHRÖTER, Methoden der organischen Chemie (Methods of Organic Chemistry), Houben-Weyl, Volume XI/1, 360 and in the examples.

The compounds of formula (I) can also be prepared by the action of a derivative of formula:

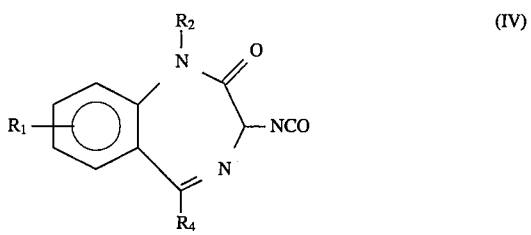

in which $R_1$, $R_2$ and $R_4$ have the same meanings as in the formula (I), on an amine of formula (III) or, when $R_3$ comprises a COOH, $PO_3H_2$, $SO_2H$ or $SO_3H$ radical, a salt of such a compound.

This reaction is generally carried out in an inert solvent such as tetrahydrofuran, dimethylformamide, a chlorinated solvent (chloroform or 1,2-dichloroethane, for example) or an aromatic solvent (benzene or toluene, for example), at a temperature of between 10° C. and the boiling point of the solvent.

The derivatives of formula (IV) can be obtained by the action of a derivative of formula (II) on a reactive derivative of carbonic acid such as phosgene, trichloromethyl chloroformate or bis(trichloromethyl) carbonate.

This reaction is carried out in an inert solvent such as toluene, at a temperature of between −30° C. and 110° C.

The compounds of formula (I), with the exception of those for which $R_3$ represents either a phenyl radical substituted by -alk-$PO_3H_2$, —CH=NOH, —CH=NO-alk-COOX, —S-alk-COOX, —SO-alk-COOX, —$SO_2$-alk-COOX, —CH=CH—COOX, -alk-CO—NHOH, -alk-N(OH)—CO-alk, —C(=NOH)—COOX, —C(COOX)=NO-alk-COOX, -alk-$SO_2H$ or tetrazolylalkyl, or a cyclic system of formula (A) in which $R_9$ represents an =NOX, =NO-alk-COOX, =CH—COOX, -alk-COOX or -alk-$SO_2H$ radical and X represents a hydrogen atom, can also be prepared by the action of a derivative of formula (II) on an isocyanate of formula:

OCN—$R_3$ (V)

in which $R_3$ has the same meanings as above.

This reaction is generally carried out in an inert solvent such as tetrahydrofuran, dimethylformamide, a chlorinated solvent (chloroform or 1,2-dichloroethane, for example) or an aromatic solvent (benzene or toluene, for example), at a temperature of between 10° C. and the boiling point of the solvent.

The isocyanates of formula (V) can be obtained by application or adaptation of the method described by R. RICHTER et al., The Chemistry of Cyanate and their Thio Derivatives, S. PATAI, part 2, Wiley New York (1977) and the methods described in the examples.

The compounds of formula (I) for which $R_3$ represents a phenyl radical substituted by an —SO-alk-COOX or $SO_2$-alk-COOX radical and X represents an alkyl radical can be prepared by oxidation of corresponding compounds of formula (I) for which $R_3$ represents a phenyl radical substituted by an —S-alk-COOX radical.

This oxidation is generally carried out with the aid of Oxone® (potassium peroxymonosulphate) marketed by Aldrich, in an alcohol such as methanol or a methanol/water mixture, at a temperature near to 25° C.

The compounds of formula (I) for which $R_3$ represents either a phenyl radical substituted by —CH=N—O-alk-COOX, —S-alk-COOX, —SO-alk-COOX, —C(=NOH)—COOX, —$SO_2$-alk-COOX, —CH=CH—COOX or —C(COOH)=N—O—alk-COOX, or a cyclic system of formula (A) in which $R_9$ represents a radical =CH-COOX, =NO-alk-COOX or -alk-COOX and X represents a hydrogen atom, can also be prepared by cleavage of a corresponding eater.

This cleavage is carried out by any method known to the person skilled in the art for converting an ester to an acid. When an alkyl ester is used, it is advantageous to work with the aid of a base such as lithium hydroxide, sodium hydroxide or potassium hydroxide, in an inert solvent such as tetrahydrofuran, dioxane, pyridine, water, an alcohol or a mixture of these solvents, at a temperature of between 20° C. and the boiling point of the solvent, or with the aid of trifluoroacetic acid, optionally in an inert solvent such as a chlorinated solvent (dichloromethane, chloroform or 1,2-dichloroethane, for example), at a temperature of between 20° C. and the boiling point of the solvent. When a benzyl ester is used, it is advantageous to work with the aid of hydrogen, in the presence of a transition metal, in an inert solvent such as an alcohol, at a temperature of between 20° and 40° C. or according to the method described by T. TSUJI et al., Tetrahedron Letters, 2793 (1979).

The compounds of formula (I) for which $R_3$ represents a cyclic system (A) in which $R_9$ represents an =NOX or =NO-alk-COOX radical can also be prepared by the action of a derivative of formula:

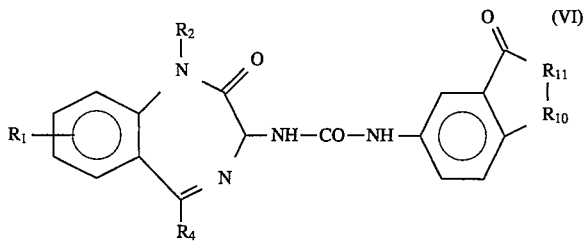

in which $R_1$, $R_2$, $R_4$, $R_{10}$ and $R_{11}$ have the same meanings as in the formula (I), on a derivative of formula:

$H_2NOZ$ (VII)

in which Z represents a hydrogen atom or an alkyl or -alk-COOX radical.

This reaction is preferably carried out in a solvent such as pyridine, water or a mixture of these solvents, at the boiling point of the reaction medium.

It is understood by the person skilled in the art that for the purpose of carrying out the processes according to the invention described above it may be necessary to introduce amino, hydroxyl or carboxyl protective groups in order to avoid secondary reactions such as those described by T. W. GREENE, Protective Groups in Organic Synthesis, John Wiley, New York. The amino functions can be blocked, for example, in the form of tert-butyl or methyl carbamates and then regenerated with the aid of iodotrimethylsilane or in the form of benzyl carbamates and then regenerated by hydrogenation after having carried out the process according to the invention. The hydroxyl functions can be blocked, for example, in the form of benzoate and then regenerated by hydrolysis in alkaline medium after having carried out the process according to the invention.

The enantiomers of the compounds of formula (I) containing at least one asymmetric site can be obtained by resolution of the racemates, for example by chromatography on a chiral column according to W. H. PIRKLE et al., Asymmetric Synthesis, Vol. 1, Academic Press (1983) or on a silica column coated with cellulose tris(3,5-dimethylphenylcarbamate) such as those described in J. Am Chem. Soc., 106, 5357 (1984), eluting with a suitable solvent such as ethanol or an ethanol/hexane mixture or by synthesis starting from chiral precursors.

The compounds of formula (I) can be purified by the usual known methods, for example by crystallization, chromatography or extractions.

The compounds of formula (I) can optionally be converted into addition salts with an inorganic or organic acid by the action of such an acid in an organic solvent such as an alcohol, a ketone, an ether or a chlorinated solvent.

The compounds of formula (I) containing an acidic radical can also be converted into metallic salts or into addition salts with nitrogen bases according to methods known per se. These salts can be obtained by the action of a metallic base (alkaline or alkaline earth metal, for example), ammonia, a tetraalkylammonium, an amine or a salt of an organic acid on a compound of formula (I), in a solvent. The salt formed is separated by the usual methods.

These salts are also a part of the invention.

Examples of pharmaceutically acceptable salts which can be mentioned are addition salts with inorganic or organic acids (such as the acetates, propionates, succinates, benzoates, fumarates, maleates, oxalates, methanesulphonates, isethionates, theophyllineacetates, salicylates, methylene-bis-β-oxynaphthoates, hydrochlorides, sulphates, nitrates and phosphates), salts with alkali metals (sodium, potassium or lithium) or with alkaline earth metals (calcium or magnesium), the ammonium salts or the salts of nitrogen bases (ethanolamine, trimethylamine, methylamine, benzylamine, N-benzyl-β-phenethylamine, choline, arginine, leucine, lysine or N-methylglucamine).

The compounds of formula (I) have pharmcologically interesting properties. These compounds have a strong affinity for cholecystokinin (CCK) and gastrin receptors and are thus useful in the treatment and prevention of disorders connected with CCK and gastrin at the level of the nervous system and the gastrointestinal system.

These compounds can thus be used for the treatment or prevention of psychoses, anxiety disorders, panic attacks, Parkinson's disease, tardive dyskinesia, irritable bowel syndrome, acute pancreatitis, ulcers, intestinal motility disorders, certain tumors sensitive to CCK, as an appetite regulator, in weaning from chronic treatments and alcohol or drug abuse and to control the constriction of the pupil of the eye.

These compounds also have a potentiating effect on the analgesic activity of narcotic and non-narcotic medicaments. In addition, they can have an analgesic effect of their own.

Among other things, the compounds having a strong affinity for CCK receptors modify memorization capacities. As a consequence, these compounds can be efficacious in memory disorders.

The affinity of the compounds of formula (I) for CCK receptors has been determined according to a technique inspired by that of A. SAITO et al., (J. Neuro. Chem., 37, 483–490 (1981) at the cerebral cortex level and the pancreas level.

In these tests, the $IC_{50}$ of the compounds of formula (I) is generally less than or equal to 1000 nM.

Amongst other things, it is known that the products which recognize the central CCK receptors have a similar specificity for the gastrin receptors in the gastrointestinal tract (BOCK et al., J. Med. Chem., 32, 16–23 (1989); REYFELD et al., Am. J. Physiol., 240, G255–266 (1981); BEINFELD et al., Neuropeptides, 3, 411–427 (1983)).

The compounds of formula (I) have a low toxicity. Their $LD_{50}$ is generally greater than 40 mg/kg subcutaneously in the mouse.

Of particular interest are the compounds of formula (I) for which $R_1$ represents a hydrogen atom, $R_2$ represents an alkyl radical or $—CH(R_5)COR_6$ in which $R_5$ represents a hydrogen atom and $R_6$ represents an $—NR_7R_8$ radical in which $R_7$ and $R_8$, together with the nitrogen atom to which they are attached, form a heterocycle and in particular a 1-pyrrolidinyl or piperidino cyclic system optionally substituted by one or more alkyl radicals, $R_3$ represents (a) a phenyl radical substituted by one or more substituents chosen from amongst the radicals -alk-$SO_3H$, -alk-$PO_3H_2$, —CH=NOH, —CH=NO-alk-COOX, —S-alk-COOX, —SO-alk-COOX, —$SO_2$-alk-COOX, —CH=CH—COOX, -alk-CO—NHOH, —C(=NOH)—COOX, -alk-N(OH)—CO-alk, -alk-$SO_2H$, —CH=CH-$SO_3H$, —C(COOX)=N—O—alk-COOX, tetrazolylalkyl, or a group of formula:

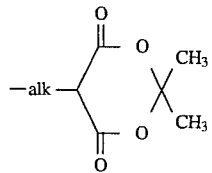

or (b) a cyclic system of formula:

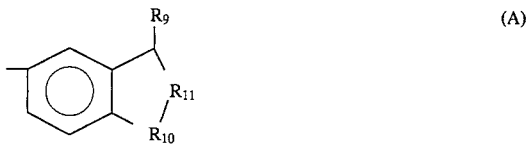

in which $R_9$ represents an =NOX, =NO-alk-COOX, =CH—COOX, -alk-COOX, -alk-$SO_2H$ or -alk-$SO_3H$ radical, $R_{10}$ represents an oxygen or sulphur atom or a methylene or alkylamino radical and $R_{11}$ represents a methylene or ethylene radical and $R_4$ represents a phenyl radical.

The following compounds are of particular interest:

(RS)-{3-{3-[2,3-dihydro-2-oxo-5-phenyl-1-(1-pyrrolidinylcarbonylmethyl)-1H-1,4-benzo[f]diazepin-3-yl]ureido}phenylthio}acetic acid, (RS)-3-[3-(2,3-dihydro-1-methyl-2-oxo-5-phenyl-1H-1,4-benzo[f]diazepin-3-yl)ureido]phenylmethanesulphonic acid, (RS)-3-{3-[1-(N-methyl-N-phenylcarbamoylmethyl)-2-oxo-5-phenyl-2,3-dihydro-1H-1,4-benzo[f]diazepin-3-yl]-3-phenyl-2(E)propenoic acid, (RS)-{3-{3-[2,3-dihydro-2-oxo-5-phenyl-1-(3,3-dimethylpiperidino)carbonylmethyl-1H-1,4-benzo[f]diazepin-3-yl]ureido}phenylthio}acetic acid, (RS)-{3-{3-[1-(N,N-diethylcarbamoylmethyl)-2,3-dihydro-2-oxo-5-phenyl-1H-1,4-benzo[f]diazepin-3-yl]ureido}phenylthio}acetic acid, (E)-(RS)-N-(2,3-dihydro-1-methyl-2-oxo-5-phenyl-1H-1,4-benzo[f]diazepin-3-yl)-N'-(1-hydroxyimino-6-indanyl)urea, (E)-(RS)-2-{3,4-dihydro-6-[3-(2,3-dihydro-1-methyl-2-oxo-5-phenyl-1H-1,4-benzo[f]diazepin-3-yl)ureido]-4-2H-benzopyranylidene}acetic acid, (E)-(RS)-3-{3-[2,3-dihydro-2-oxo-5-phenyl-1-(1-pyrrolidinyl)carbonylmethyl-1H-1,4-benzo[f]diazepin-3-yl]ureido}-2-phenylmethyleneaminooxyacetic acid, (RS)-2-{3-{3-[2,3-dihydro-2-oxo-5-phenyl-1-(1-pyrrolidinyl)carbonylmethyl-1H-1,4-benzo[f]diazepin-3-yl]ureido}phenyl}-2-(carboxymethyloxyimino)acetic acid, (RS)-5-{3-{3-[2,3-dihydro-2-oxo-5-phenyl-1-(1-pyrrolidinyl)carbonylmethyl-1H-1,4-benzo[f]diazepin-3-yl]ureido}benzyl}-2,2-dimethyl-1,3-dioxane-4,6-dione, (E)-(RS)-2-{3-{3-[1-(N,N-diethylcarbamoylmethyl)-2,3-dihydro-2-oxo-5-phenyl-1H-1,4-benzo[f]diazepin-3-yl]ureido}phenyl}ethylenesulphonic acid, (RS)-5-{3-{3-[1-(N,N-diethylcarbamoylmethyl)-2,3-dihydro-2-oxo-5-phenyl-1H-1,4-benzo[f]diazepin-3-yl]ureido}benzyl}tetrazole, (E)-(RS)-3-{3-[1-(N,N-diethylcarbamoylmethyl)-2,3-dihydro-2-oxo-5-phenyl-1H-1,4-benzo[f]diazepin-3-yl]ureido}-alpha-hydroxyiminophenylacetic acid, (RS)-{3-{3-[1-(N,N-diethylcarbamoylmethyl)-2,3-dihydro-5-(2-fluorophenyl)-2-oxo-1H-1,4-benzo[f]diazepin-3-yl]ureido}phenylthio}acetic acid, (RS)-{4-{3-[2,3-dihydro-1-(3,3-dimethylpiperidino)carbonylmethyl-2-oxo-5-phenyl-1H-1,4-benzo[f]diazepin-3-yl]ureido}phenylthio}acetic acid, (E)-(RS)-3-{3-{3-[2,3-dihydro-2-oxo-5-phenyl-1-(3,3-dimethylpiperidino)carbonylmethyl-1H-1,4-benzo[f]diazepin-3-yl]ureido}phenyl}-2-propenoic acid, (RS)-{4-{3-[2,3-dihydro-2-oxo-5-phenyl-1-(1-pyrrolidinyl)carbonylmethyl-1H-1,4-benzo[f]diazepin-3-yl]ureido}phenylthio}acetic acid, potassium (RS)-1-{3-[3-(RS)-2,3-dihydro-2-oxo-5-phenyl-1-methyl-1H-1,4-benzo[f]diazepin-3-yl)ureido]phenyl}ethanesulphonate, (+)-{3-{3-[2,3-dihydro-2-oxo-5-phenyl-1-(1-pyrrolidinyl)carbonylmethyl-1H-1,4-benzo[f]diazepin-3-yl]ureido}phenylthio}acetic acid, (−)-{3-{3-[2,3-dihydro-2-oxo-5-phenyl-1-(1-pyrrolidinyl)carbonylmethyl-1H-1,4-benzo[f]diazepin-3-yl]ureido}phenylthio}acetic acid, (RS)-{3-{3-[(RS)-2,3-dihydro-2-oxo-5-phenyl-1-(1-pyrrolidinyl)carbonylmethyl-1H-1,4-benzo[f]diazepin-3-yl]ureido}phenylsulphinyl}acetic acid, (RS)-{3-{3-[2,3-dihydro-2-oxo-5-phenyl-1-(1-pyrrolidinyl)carbonylmethyl-1H-1,4-benzo[f]diazepin-3-yl]ureido}phenylsulphonyl}acetic acid, (RS)-2-{3-{3-[(RS)-2,3-dihydro-2-oxo-5-phenyl-1-(1-pyrrolidinyl)carbonylmethyl-1H-1,4-benzo[f]diazepin-3-yl]ureido}phenylthio}propionic acid.

EXAMPLES

The following examples illustrate the invention without limiting it.

EXAMPLE 1

A solution of 1 g of tert-butyl (RS)-{3-{3-[2,3-dihydro-2-oxo-5-phenyl-1-(1-pyrrolidinyl)-carbonylmethyl-1H-1,4-benzo[f]diazepin-3-yl]ureido}phenylthio}acetate in 4 cm$^3$ of trifluoroacetic acid is stirred at a temperature near to 20° C. for 20 hours and then poured into 200 cm$^3$ of iced water. The solid is separated by filtration and rinsed with 20 cm$^3$ of water and then 20 cm$^3$ of diisopropyl ether. After recrystallization in ethanol, 0.65 g of (RS)-{3-{3-[2,3-dihydro-2-oxo-5-phenyl-1-(1-pyrrolidinyl)-carbonylmethyl-1H-1,4-benzo[f]diazepin-3-yl]ureido}-phenylthio}acetic acid melting at 168° C. is obtained.

tert-Butyl (RS)-{3-{3-[2,3-dihydro-2-oxo-5-phenyl-1-(1-pyrrolidinylcarbonylmethyl)-1H-1,4-benzo[f]diazepin-3-yl]ureido}phenylthio}acetate can be obtained in the following manner: a solution of 2.6 g of tert-butyl (3-isocyanatophenylthio)acetate in 10 cm$^3$ of tetrahydrofuran is added, at a temperature near to 20° C., to a solution of 3.2 g of (RS)-3-amino-2,3-dihydro-2-oxo-5-phenyl-1-(1-pyrrolidinyl)carbonylmethyl-1H-1,4-benzo[f]diazepine in 40 cm$^3$ of tetrahydrofuran. The mixture is stirred for 70 hours at a temperature near to 20° C. and then concentrated to dryness under reduced pressure (2.7 kPa) at 40° C. The residue is dissolved in 30 cm$^3$ of dimethylformamide. The solution is poured into 200 cm$^3$ of iced water and the solid is filtered, dried and chromatographed on 200 cm$^3$ of silica (eluent: ethyl acetate). The fractions containing the expected product are combined and concentrated to dryness under reduced pressure (2.7 kPa). 3.9 g of tert-butyl (RS)-{3-{3-[2,3-dihydro-2-oxo-5-phenyl-1-(1-pyrrolidinyl)carbonylmethyl-1H-1,4-benzo[f]diazepin-3-yl]ureido}phenylthio}acetate are obtained in the form of an amorphous solid which is used as such in the subsequent syntheses.

(RS)-3-Amino-2,3-dihydro-2-oxo-5-phenyl-1-(1-pyrrolidinyl)carbonylmethyl-1H-1,4-benzo[f]diazepine can be obtained in the following manner: a solution of 5.1 g of 2,3-dihydro-3-hydroxyimino-2-oxo-5-phenyl-1-(1-pyrrolidinyl)carbonylmethyl-1H-1,4-benzo[f]diazepine in 50 cm$^3$ of methanol is added to a suspension of 1 g of 5% ruthenium on carbon in 35 cm$^3$ of methanol. The mixture is stirred for 30 hours at a temperature near to 70° C. under a hydrogen atmosphere (500 kPa). The catalyst is separated by filtration and the filtrate is concentrated under reduced pressure (2.7 kPa). The residue is dissolved in 100 cm$^3$ of dichloromethane and extracted with 3 times 50 cm$^3$ of a normal aqueous solution of hydrochloric acid. The aqueous phases are combined and brought to a pH near to 9 by addition of sodium hydrogencarbonate and then extracted with 3 times 100 cm$^3$ of dichloromethane. The organic phases are combined, dried over magnesium sulphate, filtered and concentrated under reduced pressure (2.7 kPa). 3.25 g of (RS)-3-amino-2,3-dihydro-2-oxo-5-phenyl-1-(1-pyrrolidinyl)carbonylmethyl-1H-1,4-benzo[f]diazepine are obtained in the form of a solid foam which is used as such in the subsequent syntheses.

2,3-Dihydro-3-hydroxyimino-2-oxo-5-phenyl-1-(1-pyrrolidinyl)carbonylmethyl-1H-1,4-benzo[f]diazepine can be prepared in the following manner: 9 g of 2,3-dihydro-2-oxo-5-phenyl-1-(1-pyrrolidinyl)carbonylmethyl-1H-1,4-benzo[f]diazepine are added, at a temperature near to −20° C., to a solution of 7.27 g of potassium tert-butoxide in 50 cm$^3$ of tert-butanol and 150 cm$^3$ of tetrahydrofuran, in portions, in the course of 50 minutes. The suspension is stirred for 3 hours at a temperature below −20° C. and then 9.8 cm$^3$ of isopentyl nitrite are added. The suspension is again stirred for 1 hour at a temperature near to 0° C. and then 5 cm$^3$ of acetic acid and 10 cm$^3$ of water are added. After returning to a temperature near to 20° C., the precipitate is filtered and washed with pentane. After recrystallization in ethanol, 3.17 g of 2,3-dihydro-3-hydroxyimino-2-oxo-5-phenyl-1-(1-pyrrolidinyl)carbonylmethyl-1H-1,4-benzo [f]diazepine are thus obtained, melting above 260° C.

2,3-Dihydro-2-oxo-5-phenyl-1-(1-pyrrolidinyl) carbonylmethyl-1H-1,4-benzo [f]diazepine is obtained in the following manner: a suspension of 25 g of 2,3-dihydro-2-oxo-5-phenyl-1H-1,4-benzo [f]diazepine, 20.5 g of 1-chloroacetylpyrrolidine, 14.6 g of potassium carbonate and 17.6 g of potassium iodide in 250 cm³ of dimethylformamide is stirred for 170 hours at a temperature near to 25° C. The reaction mixture is poured into 1500 cm³ of iced water. The aqueous phase is separated from the insoluble matter and extracted with 3 times 300 cm³ of ethyl acetate. The organic extracts are combined, washed with 200 cm³ of a saturated aqueous solution of sodium chloride, dried over magnesium sulphate, filtered and concentrated to dryness under reduced pressure (2.7 kPa) at a temperature near to 45° C. After crystallization in ethyl acetate, 14.7 g of 2,3-dihydro-2-oxo-5-phenyl-1-(1-pyrrolidinyl)-carbonylmethyl-1H-1,4-benzo [f]diazepine are obtained, melting at 190° C.

tert-Butyl (3-isocyanatophenylthio)acetate can be obtained in the following manner: a solution of 2.9 g of tert-butyl (3-aminophenylthio)acetate in 25 cm³ of toluene is added dropwise, at a temperature near to −30° C., to a suspension of 0.24 g of carbon in 1.46 cm³ of trichloromethyl chloroformate and 15 cm³ of toluene. The reaction mixture is stirred for 2 hours at a temperature near to 20° C. and then for 2 hours and 30 minutes at a temperature near to 110° C. The reaction mixture is then cooled to a temperature near to 20° C., degassed by bubbling nitrogen in, filtered and then concentrated to dryness under reduced pressure (2.7 kPa) at 50° C. 2.6 g of tert-butyl (3-isocyanatophenylthio)acetate are thus obtained in the form of an oil which is used as such in the subsequent syntheses.

tert-Butyl (3-aminophenylthio)acetate can be prepared in the following manner: a solution of 25 g of 3-aminothiophenol and 39 g of tert-butyl bromoacetate in 400 cm³ of ethanol is stirred for 3 hours at a temperature near to 25° C. and then concentrated under reduced pressure (2.7 kPa). The residue is dissolved in 500 cm³ of ethyl acetate. The solution is washed successively with 3 times 75 cm³ of a normal aqueous solution of sodium hydroxide and 3 times 75 cm³ of a saturated aqueous solution of sodium chloride and is concentrated under reduced pressure (2.7 kPa). The residue is then purified by chromatography on 800 cm³ of silica (eluent: cyclohexane/ethyl acetate (90:10 and then 80:20 by volume)). The fractions containing the expected products are combined and concentrated under reduced pressure (2.7 kPa). 24 g of tert-butyl (3-aminophenylthio)acetate are obtained in the form of an oil which is used as such in the subsequent syntheses.

1-Chloroacetylpyrrolidine can be prepared according to the method described by A. J. SPEZIALE et al., J. Am. Chem. Soc., 78, 2556 (1956).

2,3-Dihydro-2-oxo-5-phenyl-1H-1,4-benzo [f]diazepine can be prepared by the method described by L. H. STERNBACH et al., J. Org. Chem., 27, 3788 (1962).

EXAMPLE 2

A solution of 2.65 g of (RS)-3-amino-2,3-dihydro-1-methyl-2-oxo-5-phenyl-1H-1,4-benzo [f]diazepine in 50 cm³ of 1,2-dichloroethane is added at a temperature near to 25° C. to a solution of 1.8 g of N,N'-carbonyldiimidazole in 30 cm³ of 1,2-dichloroethane. The reaction mixture is stirred for 3 hours at a temperature near to 25° C. and then a solution of 4.3 g of tetrabutylammonium 3-aminophenylmethanesulphonate in 70 cm³ of 1,2-dichloroethane is added. The reaction mixture is stirred at a temperature near to 80° C. for 18 hours and then cooled to a temperature near to 25° C. and diluted with 150 cm³ of dichloromethane, washed with two times 100 cm³ of water, dried over magnesium sulphate, filtered and concentrated to dryness under reduced pressure (2.7 kPa) at 60° C. A fraction of 2.8 g of the residue is purified by chromatography on 60 cm³ of silica contained in a column of diameter 2 cm (eluent: dichloromethane/methanol (97:3 by volume)). The residue is dissolved in 50 cm³ of methanol and treated with 10 g of acidic resin (IR 120). The suspension is filtered and washed with 3 times 50 cm³ of methanol and then the filtrate is concentrated under reduced pressure and the residue is triturated in 50 cm³ of diethyl ether, filtered and washed with two times 25 cm³ of diethyl ether. 0.9 g of (RS)-3-[3-(2,3-dihydro-1-methyl-2-oxo-5-phenyl-1H-1,4-benzo [f]diazepin-3-yl)ureido]phenylmethanesulphonic acid melting at 230° C. is thus obtained.

Tetrabutylammonium 3-aminophenylmethanesulphonate can be prepared in the following manner: 1 g of 5% of palladium on carbon is added to a solution of 41.4 g of tetrabutylammonium 3-nitrophenylmethanesulphonate in 300 cm³ of ethanol. The suspension is stirred for 2 hours at a temperature near to 20° C. under a hydrogen atmosphere (128 kPa). The catalyst is separated by filtration and the filtrate is concentrated to dryness under reduced pressure (2.7 kPa) at 50° C. 42.2 g of tetrabutylammonium 3-aminophenylmethanesulphonate are thus obtained in the form of an oil which is used as such in the subsequent syntheses.

Tetrabutylammonium 3-nitrophenylmethanesulphonate can be prepared in the following manner: 6.9 g of sodium 3-nitrophenylmethanesulphonate and then 9.9 g of tetrabutylammonium hydrogensulphate are added to 800 cm³ of an aqueous solution of 0.5M potassium dihydrogenphosphate. The mixture is extracted with 500 cm³ of methylene chloride. The organic phase is dried over magnesium sulphate and concentrated to dryness under reduced pressure at 40° C. 13 g of tetrabutylammonium 3-nitrophenylmethanesulphonate are thus obtained in the form of an oil which is used as such in the subsequent syntheses.

Sodium 3-nitrophenylmethanesulphonate can be prepared according to the technique described by PURGOTTI et al., Gazz. Chim. Ital., 30, II, 247.

(RS)-3-Amino-2,3-dihydro-1-methyl-2-oxo-5-phenyl-1H-1,4-benzo[f]diazepine can be obtained according to the technique described by M.G. BOCK et al., J. Org. Chem., 52, 3232 (1987).

EXAMPLE 3

3.4 cm³ of a normal aqueous solution of sodium hydroxide are added to a suspension of 1.7 g of ethyl (E)-(RS)-3-{3-[1-(N-methyl-N-phenylcarbamoylmethyl-2-oxo-5-phenyl-2,3-dihydro-1H-1,4-benzo[f]diazepin-3-yl]ureido}-3-phenyl-2-propenoate in 6 cm³ of ethanol and the mixture is brought to a temperature near to 80° C. in the course of 30 minutes. After cooling to a temperature near to 20° C., 20 cm³ of water are added and the mixture is then washed with 50 cm³ of ethyl acetate. The aqueous phase is acidified to pH 1 with 4 cm³ of a normal aqueous solution of hydrochloric acid. After extraction with 50 cm³ of dichloromethane, the organic phase is dried over magnesium sulphate and concentrated under reduced pressure (2.7 kPa). 0.6 g of (RS)-3-{3-[1-(N-methyl-N-phenylcarbamoylmethyl)-2-oxo-5- phenyl-2,3-dihydro-1H-1,4-benzo[f]diazepin-3-yl]-3-phenyl-2(E)propanoic acid melting at 180° C. is obtained after recrystallization in diisopropyl ether.

Ethyl (E)-(RS)-3-{3-[1-(N-methyl-N-phenylcarbamoyl-methyl)-2-oxo-5-phenyl-2,3-dihydro-1H-1,4-benzo[f]diazepin-3-yl]ureido}-3-phenyl-2- propenoate can be prepared in the following manner: a solution of 0.85 g of ethyl (E)-3-(3- isocyanatophenyl)-2-propenoate in 10 cm³ of tetrahydrofuran is added under an inert atmosphere at a temperature near to 20° C. in the course of 15 minutes to a solution of 1.57 g of (RS)-2-(3-amino-2,3-dihydro-2-oxo-5-phenyl-1H-1,4-benzo[f]diazepin-1-yl)-N-methylacetanilide in 20 cm³ of tetrahydrofuran. The reaction mixture is stirred at a temperature near to 20° C. for 4 hours. After concentration to dryness under reduced pressure (2.7 kPa) at 50° C., the residue is dissolved in 10 cm³ of ethyl acetate and then diluted with 30 cm³ of diethyl ether. 1.7 g of (E)-(RS)-3-{3-[1-(N-methyl-N-phenylcarbamoylmethyl)-2-oxo-5-phenyl-2,3-dihydro-1H-1,4-benzo[f]diazepin-3-yl]ureido}-3-phenyl-2-propenoate melting at 238° C. are thus obtained.

Ethyl (E)-3-(3-isocyanatophenyl)-2-propenoate can be prepared in the following manner: a suspension of 0.15 g of carbon in a solution of 1 g of bis(trichloromethyl) carbonate in 10 cm³ of toluene is cooled to a temperature near to −20° C. under an inert atmosphere. A solution of 1.2 g of ethyl (E)-metaaminocinnamate in 10 cm³ of toluene is run in in the course of 15 minutes keeping the temperature at −20° C. The reaction mixture is stirred for 2 hours at a temperature near to 20° C. and then for 2 hours 30 minutes at a temperature near to 110° C. The reaction mixture is cooled to a temperature near to 20° C., the black matter is filtered on Clarcel, rinsed with 20 cm³ of dichloromethane and concentrated under reduced pressure (2.7 kPa) to obtain 1.35 g of ethyl (E)-3-(3-isocyanatophenyl)-2-propenoate in the form of an oil which is used as such in the subsequent syntheses.

(RS)-2-(3-Amino-2,3-dihydro-2-oxo-5phenyl-1H-1,4-benzo[f]diazepin-1-yl)-N-methylacetanilide can be prepared in the following manner: a suspension of 10 g of Raney nickel in a solution of 5.3 g of 2-(2,3-dihydro-3-hydroxyimino-2-oxo-5-phenyl-1H-1,4-benzo[f]diazepin-1-yl)-N-methylacetanilide in 75 cm³ of methanol is stirred for 24 hours at a temperature near to 20° C. under a hydrogen atmosphere (1.5 MPa). The catalyst is separated by filtration and the filtrate is concentrated under reduced pressure (2.7 kPa) at 35° C. The residue is purified by chromatography on 400 cm³ of silica contained in a column of diameter 4 cm (eluents: dichloromethane and then dichloromethane/methanol (98:2 and then 95:5 by volume)). The fractions containing the expected product are combined and concentrated under reduced pressure (2.7 kPa). 1 g of (RS)-2-(3-amino-2,3-dihydro-2-oxo-5-phenyl-1H-1,4-benzo[f]diazepin-1-yl)-N-methylacetanilide melting at 80° C. is thus obtained.

2-(2,3-Dihydro-3-hydroxyimino-2-oxo-5-phenyl-1H-1,4-benzo[f]diazepin-1-yl)-N-methylacetanilide can be prepared in a manner analogous to that described in Example 1 for the preparation of 2,3-dihydro-3-hydroxyimino-2-oxo-5-phenyl-1-(1-pyrrolidinyl)carbonylmethyl-1H-1,4-benzo[f]diazepine but starting from 5.04 g of potassium tert-butoxide, 30 cm³ of tert-butanol, 130 cm³ of tetrahydrofuran, 6.5 g of 2-(2,3-dihydro-2-oxo-5-phenyl-1H-1,4-benzo[f]diazepin-1-yl)-N-methylacetanilide and 3.2 cm³ of isopentyl nitrite. 5.3 g of 2-(2,3-dihydro-3-hydroxyimino-2-oxo-5-phenyl-1H-1,4-benzo[f]diazepin-1-yl)-N-methylacetanilide are obtained in the form of a solid foam which is used as such in the subsequent syntheses.

2-(2,3-Dihydro-2-oxo-5-phenyl-1H-1,4-benzo[f]diazepin-1-yl)-N-methylacetanilide can be obtained in a manner analogous to that described in Example 1 for the preparation of 2,3-dihydro-2-oxo-5-phenyl-1-(1-pyrrolidinyl)carbonylmethyl-1H-1,4-benzo[f]diazepine, but starting from 4.6 g of N-methyl-2-bromoacetanilide, 4.7 g of 2,3-dihydro-2,3-dihydro-2-oxo-5-phenyl-1H-1,4-benzo[f]diazepine, 3.5 g of potassium carbonate and 50 cm³ of dimethylformamide. 8 g of 2-(2,3-dihydro-2-oxo-5-phenyl-1H-1,4-benzo[f]diazepin-1-yl)-N-methylacetanilide are thus obtained which are used as such in the subsequent syntheses.

N-Methyl-2-bromoacetanilide can be prepared in the following manner: 11.1 g of triethylamine and a solution of 20.4 g of bromoacetyl bromide in 10 cm³ of dichloromethane are added successively, at temperature near to −5° C., to a solution of 10.7 g of N-methylaniline in 65 cm³ of dichloromethane. The suspension is stirred for 2 hours at a temperature near to 20° and 25 cm³ of water are then added. The aqueous phase is separated by decantation and reextracted with two times 15 cm³ of dichloromethane. The organic phases are combined, washed with 3 times 25 cm³ of water, dried over magnesium sulphate, filtered and then concentrated to dryness under reduced pressure (2.7 kPa) at 40° C. 100 cm³ of diethyl ether are added to the residual oil; the insoluble product is separated by filtration and washed with 3 times 15 cm³ of diethyl ether. The filtrates are combined and concentrated to dryness under reduced pressure (2.7 kPa) at 40° C. 20.5 g of N-methyl-2-bromoacetanilide are thus obtained in the form of an oil which is used as such in the subsequent syntheses.

Ethyl (E)-meta-aminocinnamate can be obtained by the method described in the Patent Application NL 7,416,449 (C.A., 84, 58882q).

EXAMPLE 4

Working as in Example 1, but starting from 1.5 g of tert-butyl (RS)-{3-{3-[2,3-dihydro-2-oxo-5-phenyl-1-(3,3-dimethylpiperidino)carbonylmethyl-1H-1,4-benzo[f]-diazepin-3-yl]ureido}phenylthio}acetate and 5.5 cm³ of trifluoroacetic acid, 0.55 g of (RS)-{3-{3-[2,3-dihydro-2-oxo-5-phenyl-1-(3,3-dimethylpiperidino)carbonylmethyl-1H-1,4-benzo[f]diazepin-3-yl]ureido}phenylthio}acetic acid melting at 240° C. is obtained.

tert-Butyl (RS)-{3-{3-[2,3-dihydro-2-oxo-phenyl-1-(3,3-dimethylpiperidino)carbonylmethyl-1H-1,4-benzo[f]diazepin-3-yl]ureido}phenylthio}acetate can be prepared in a manner analogous to that described in Example 1 for the preparation of tert-butyl (RS)-{3-{3-[2,3-dihydro-2-oxo-5-phenyl-1-(1-pyrrolidinyl)carbonylmethyl-1H-1,4-benzo[f] diazepin-3-yl]ureido}phenylthio}acetate, but starting from 1.65 g of (RS)-3-amino-2,3-dihydro-2-oxo-5-phenyl-1-(3,3-dimethylpiperidino)carbonylmethyl-1H-1,4-benzo[f]diazepine and 1.13 g of tert-butyl (3-isocyanatophenylthio)acetate in 35 cm³ of tetrahydrofuran. 1.57 g of tert-butyl (RS)-{3-{3-[2,3-dihydro-2-oxo-phenyl-1-(3,3-dimethylpiperidino)carbonylmethyl-1H-1,4-benzo[f]diazepin-3-yl]ureido}-phenylthio}acetate melting at 110° C. are thus obtained.

(RS)-3-Amino-2,3-dihydro-2-oxo-5-phenyl-1-(3,3-dimethylpiperidino)carbonylmethyl-1H-1,4-benzo[f]diazepine can be prepared in a manner analogous to that described in Example 1 for the preparation of (RS)-3-amino-2,3-dihydro-2-oxo-5-phenyl-1-(1-pyrrolidinyl)carbonylmethyl-1H-1,4-benzo[f]diazepine, but starting from 7.1 g of 2,3-dihydro-1-(3,3-dimethylpiperidino)carbonylmethyl-3-hydroxyimino-2-oxo-5-phenyl-1,4-benzo[f]diazepine and 1.8 g of 5% ruthenium on carbon in 160 cm³ of methanol.

4.95 g of (RS)-3-amino-2,3-dihydro-2-oxo-5-phenyl-1-(3,3-dimethylpiperidino)carbonylmethyl-1H-1,4-benzo[f]diazepine melting at 88° C. are thus obtained.

2,3-Dihydro-1-(3,3-dimethylpiperidino)carbonylmethyl-3-hydroxyimino-2-oxo-5-phenyl-1H-1,4-benzo[f]diazepine can be obtained in a manner analogous to that described in Example 1 for the preparation of 2,3-dihydro-3-hydroxyimino-2-oxo-5-phenyl-1-(1-pyrrolidinyl)carbonylmethyl-1H-1,4-benzo[f]diazepine, but starting from 16.5 g of 2,3-dihydro-1-(3,3-dimethylpiperidino)carbonylmethyl-2-oxo-5-phenyl-1H1,4-benzo[f]diazepine, 11.88 g of potassium tert-butoxide and 7 cm³ of isopentyl nitrite in 300 cm³ of toluene. 7 g of 2,3-Dihydro-1-(3,3-dimethylpiperidino)carbonylmethyl-3-hydroxyimino-2-oxo-5-phenyl-1H-1,4-benzo[f]diazepine melting at 145° C. are thus obtained.

2,3-Dihydro-1-(3,3-dimethylpiperidino)carbonylmethyl-2-oxo-5-phenyl-1H-1,4-benzo[f]diazepine can be prepared in the following manner: a solution of 31.9 g of (2,3-dihydro-2-oxo-5-phenyl-1H-1,4-benzo[f]diazepin-1-yl)acetic acid, 17.6 g of N,N'-carbonyldiimidazole and 0.66 g of N,N-4-dimethylaminopyridine in 250 cm³ of tetrahydrofuran is stirred for 18 hours at a temperature near to 20° C. A solution of 12.3 g of 3,3-dimethylpiperidine in 60 cm³ of tetrahydrofuran is then added and the mixture is stirred again for 5 hours 30 minutes. The reaction mixture is poured into 500 cm³ of water. The aqueous phase is extracted with 3 times 500 cm³ and then again with once 250 cm³ of diethyl ether. The organic extracts are combined, washed with 3 times 250 cm³ of water, dried over magnesium sulphate and concentrated to dryness under reduced pressure (2.7 kPa) at 40° C. The residue is purified by chromatography on 700 cm³ of silica contained in a column of diameter 6 cm (eluents: dichloromethane and then dichloromethane/methanol (98:2 by volume). The fractions containing the expected product are combined and concentrated to dryness under reduced pressure (2.7 kPa). After crystallisation in pentane, 15 g of 2,3-dihydro-1-(3,3-dimethylpiperidino)carbonylmethyl-2-oxo-5-phenyl-1H-1,4-benzo[f]diazepine melting at 86° C. are thus obtained.

(2,3-Dihydro-2-oxo-5-phenyl-1H-1,4-benzo[f]diazepin-1-yl)acetic acid can be prepared in a manner analogous to that described in Example 1 for the preparation of (RS)-{3-[2,3-dihydro-2-oxo-5-phenyl-1-(1-pyrrolidinyl)carbonylmethyl-1H-1,4-benzo[f]diazepin-3-yl]ureido}phenylythio}acetic acid, but starting from 27.7 g of tert-butyl (2,3-dihydro-2-oxo-5-phenyl-1H-1,4-benzo[f]diazepin-1-yl)acetate and 100 cm³ of trifluoroacetic acid. 21.9 g of (2,3-dihydro-2-oxo-5-phenyl-1H-1,4-benzo[f]diazepin-1-yl)acetic acid melting at 163° C. are obtained.

tert-Butyl (2,3-dihydro-2-oxo-5-phenyl-1H-benzo[f]diazepin-1-yl)acetate can be prepared in the following manner: 0.99 g of a dispersion of 60% sodium hydride in liquid paraffin is added at a temperature near to 0° C. to a solution of 0.7 g of 2,3-dihydro-2-oxo-5-phenyl-1H-1,4-benzo[f]diazepine in 5 cm³ of tetrahydrofuran. The reaction mixture is stirred for 2 hours at a temperature near to 0° C. and then a solution of 0.48 cm³ of tert-butyl bromoacetate in 5 cm³ of tetrahydrofuran is added. The reaction mixture is stirred for 2 hours at a temperature near to 17° C. and then 5 cm³ of water are added and the mixture is poured into 100 cm³ of water. The aqueous phase is extracted with 4 times 75 cm³ of ethyl acetate. The organic extracts are combined, washed with 25 cm³ of a normal aqueous solution of ammonium carbonate, dried over magnesium sulphate and brought to dryness under reduced pressure (2.7 kPa) at 40° C. After crystallization in pentane, 0.99 g of tert-butyl (2,3-dihydro-2-oxo- 5-phenyl-1H-benzo[f]diazepin-1-yl)acetate melting at 149° C. is thus obtained.

EXAMPLE 5

Working as in Example 1, but starting from 2 g of tert-butyl (RS)-{3-[1-(N,N-diethylcarbamoylmethyl)-2,3-dihydro-2-oxo-5-phenyl-1H-1,4-benzo[f]diazepin-3-yl]ureido}phenylthio}acetate and 10 cm³ of trifluoroacetic acid and recrystallizing in 60 cm³ of ethanol, 1.42 g of (RS){3-{3-[1-(N,N-diethylcarbamoylmethyl)-2,3-dihydro-2-oxo-5-phenyl-1H-1,4-benzo[f]diazepin-3-yl]ureido}phenylthio}acetic acid melting at 200° C. with decomposition are obtained.

tert-Butyl (RS)-{3-[1-(N,N-diethylcarbamoylmethyl)-2,3-dihydro-2-oxo-5-phenyl-1H-1,4-benzo[f]diazepin-3-yl]ureido}phenylthio}acetate can be obtained in the following manner: a solution of 3.1 g of (RS)-3-amino-1-(N,N-diethylcarbamoylmethyl)-2,3-dihydro-2-oxo-5-phenyl-1H-1,4-benzo[f]diazepine in 25 cm³ of tetrahydrofuran is added in the course of 10 minutes at a temperature near to 20° C. to a solution of 2.38 g of tert-butyl (3-isocyanatophenylthio)acetate in 10 cm³ of tetrahydrofuran. The mixture is stirred for 18 hours at a temperature near to 20° C. and diluted with 60 cm³ of diethyl ether. The precipitate is filtered. 3.6 g of tert-butyl (RS)-{3-[1-(N,N-diethylcarbamoylmethyl)-2,3-dihydro-2-oxo-5-phenyl-1H-1,4-benzo[f]diazepin-3-yl]ureido}phenylthio}acetate melting at 220° C. with decomposition are thus obtained.

(RS)-3-Amino-1-(N,N-diethylcarbamoylmethyl)-2,3-dihydro-2-oxo-5-phenyl-1H-1,4-benzo[f]diazepine can be obtained in the following manner: a suspension of 10.3 g of 1-(N,N-diethylcarbamoylmethyl)-2,3-dihydro-3-hydroxyimino-2-oxo-5-phenyl-1H-1,4-benzo[f]diazepine and 2 g of 5% ruthenium on carbon in 200 cm³ of methanol is stirred for 15 hours at a temperature near to 70° C. under a hydrogen atmosphere (800 kPa). The catalyst is separated by filtration and the filtrate is concentrated under reduced pressure (2.7 kPa). The residue is purified by chromatography on a column of diameter 6 cm containing 600 cm³ of silica, eluting at first with 400 cm³ of pure dichloromethane, then with 3 liters of dichloromethane/ethanol mixture (95:5 by volume) and then dichloromethane/ethanol mixture (90:10 by volume). The fractions between 1.25 and 5 liters are combined and concentrated under reduced pressure (2.7 kPa) to give 8.1 g of white solid foam. By taking up in diisopropyl ether, 7.6 g of (RS)-3-amino-1-(N,N-diethylcarbamoylmethyl)-2,3-dihydro-2-oxo-5-phenyl-1H-1,4-benzo[f]diazepine melting at 152° C. are obtained.

1-(N,N-Diethylcarbamoylmethyl)-2,3-dihydro-3-hydroxyimino-2-oxo-5-phenyl-1H-1,4-benzo[f]diazepine can be obtained in a manner analogous to that described in Example 1 for the preparation of 2,3-dihydro-3-hydroxyimino-2-oxo-5-phenyl-1-(1-pyrrolidinyl)carbonyl -methyl-1H-1,4-benzo[f]diazepine, but starting from 11.8 g of 1-(N,N-diethylcarbamoylmethyl)-2,3-dihydro-2 -oxo-5-phenyl-1H-1,4-benzo[f]diazepine, 7.6 g of potassium tert-butoxide and 5 cm³ of isopentyl nitrite in 350 cm³ of toluene. 10.42 g of 1-(N,N-diethylcarbamoylmethyl-2,3-dihydro-3-hydroxyimino-2-oxo-5-phenyl-1H-1,4-benzo[f]diazepine melting at 220° C. are thus obtained.

1-(N,N-Diethylcarbamoylmethyl)-2,3-dihydro-2-oxo-5-phenyl-1H-1,4-benzo[f]diazepine can be obtained in the following manner: 0.75 g of potassium iodide and 17.5 g of potassium carbonate are added to a solution of 10 g of 2,3-dihydro-2-oxo-5-phenyl-1H-1,4-benzo[f]diazepine and 6.65 g of N,N-diethyl-2-chloroacetamide in 100 cm³ of dimethylformamide. The suspension obtained is stirred at a temperature near to 20° C. for 16 hours. The reaction mixture is concentrated under reduced pressure (1.2 kPa).

The residue is taken up in 100 cm³ of ethyl acetate. The organic phase is washed two times with water and then dried over magnesium sulphate and concentrated to dryness under reduced pressure (2.7 kPa). The residue is purified by chromatography on a column of diameter 6 cm containing 900 cm³ of silica, eluting first with a cyclohexane/ethyl acetate mixture (50:50 by volume) and then with pure ethyl acetate and collecting fractions of 125 cm³. The fractions of between 3.75 and 4.75 liters are combined and evaporated to dryness to give 11.9 g of 1-(N,N-diethylcarbamoylmethyl)-2,3-dihydro-2-oxo-5-phenyl-1H-1,4-benzo[f]diazepine in the form of a solid foam which is used as such in the subsequent syntheses.

EXAMPLE 6

A solution of 2.5 g of (RS)-N-(2,3-dihydro-1-methyl-2-oxo-5-phenyl-1H-1,4-benzo[f]diazepin-3-yl) -N'-(1-oxo-6-indanyl)urea and 6.12 g of hydroxylamine hydrochloride in 80 cm³ of aqueous pyridine (75:25 by volume) is heated for 2 minutes to a temperature near to 100° C. The reaction mixture is cooled to a temperature near to 20° C. and concentrated under reduced pressure (2.7 kPa). It is diluted with 200 cm³ of water, acidified to pH 1 with an aqueous solution of 6N hydrochloric acid and extracted with 200 cm³ of ethyl acetate. The organic phase is washed with two times 200 cm³ of water, dried over magnesium sulphate, and then concentrated to dryness. The residue is purified by chromatography under pressure (4.1 MPa) on a column of 300 g of silica of 15–20 microns, eluting first with 3 liters of dichloromethane/methanol mixture (98:2 by volume), and then 850 cm³ of dichloromethane/methanol mixture (95:5 by volume). The fractions between 1750 and 3850 cm³ are combined and evaporated to dryness to give 1.7 g of a white solid foam. After recrystallization in 30 cm³ of ethyl acetate, 1 g of (E)-(RS)-N-(2,3-dihydro-1-methyl-2-oxo-5-phenyl-1H -1,4-benzo[f]diazepin-3-yl)-N'-(1-hydroxyimino-6-indanyl)urea melting at 218° C. is obtained.

(RS)-N-(2,3-Dihydro-1-methyl-2-oxo-5-phenyl-1H -1,4-benzo[f]diazepin-3-yl)-N'-(1-oxo-6-indanyl)urea can be obtained in the following manner: a solution of 1.9 g of 6-isocyanato-1-indanone in 20 cm³ of tetrahydrofuran is added in the course of 10 minutes to a solution of 2.5 g of 3-amino-1-methyl-2-oxo-5-phenyl-1,4-benzo[f]diazepine in 90 cm³ of tetrahydrofuran. After stirring for 15 minutes at a temperature near to 20° C., insoluble matter is filtered and washed with two times 15 cm³ of tetrahydrofuran and with two times 50 cm³ of diisopropyl ether, to obtain 3.2 g of (RS)-N-(2,3-dihydro-1-methyl-2-oxo-5-phenyl-1H-1,4-benzo[f]diazepin-3-yl)-N'-(1-oxo-6-indanyl)urea melting at about 270° C. with decomposition.

6-Isocyanato-1-indanone can be prepared in the following manner: a solution of 1.6 g of bis(trichloromethyl) carbonate in 20 cm³ of toluene is added in the course of 25 minutes to a suspension cooled to about –20° C. of 1.6 g of 6-amino-1-indanone and 0.2 g of animal charcoal in 30 cm³ of toluene, at a temperature near to –20° C. The mixture is allowed to warm up to ambient temperature, then it is heated for 2 hours at a temperature near to 110° C. The suspension obtained is cooled to a temperature near to 20° C. and filtered, and the filtrate is concentrated under reduced pressure (2.7 kPa) to give 1.9 g of 6-isocyan-ato -1-indanone melting at 72° C.

6-Amino-1-indanone can be prepared according to the method described by C. K. INGOLD and H. A. PIGGOT, J. Chem. Soc., 123, 1469 (1923).

EXAMPLE 7

70 cm³ of an aqueous solution of 0.1N sodium hydroxide are added to a solution of 1.9 g of ethyl (E)-(RS)-2-{3,4-dihydro-6-[3-(2,3-dihydro-1-methyl-2-oxo-5-phenyl-1H-1,4-benzo[f]diazepin-3-yl)ureido]-4-2H-benzopyranylidene}acetate in 40 cm³ of pyridine, and the mixture is then heated to a temperature near to 100° C. for 2 hours. After cooling to a temperature near to 20° C., the mixture is concentrated under reduced pressure (1.2 kPa). The residue is diluted with 100 cm³ of water and washed with 100 cm³ of dimethyl ether. The aqueous phase is brought to pH 1 with an aqueous solution of 4N hydrochloric acid and extracted with 100 cm³ of ethyl acetate. The organic phase is washed with 200 cm³ of water, dried over magnesium sulphate and concentrated to dryness. The residue obtained is purified by chromatography on a column of diameter 2.5 cm containing 160 cm³ of silica, eluting with 500 cm³ of dichloromethane, and then 2 liters of dichloromethane/methanol mixture (98:2 by volume) then 1 liter of dichloromethane/methanol mixture (95:5 by volume), and then 2 liters of dichloromethane/methanol mixture (93:7 by volume) and collecting fractions of 250 cm³. The fractions between 1 and 5.5 liters are combined and evaporated to dryness to give 0.33 g of a yellow solid. By recrystallization in 25 cm³ of diisopropyl ether, 0.26 g of (E)-(RS)-2-{3,4-dihydro-6-[3-(2,3-dihydro-1-methyl-2-oxo-5-phenyl-1H-1,4-benzo[f]diazepin-3-yl)ureido]-4-2H-benzopyranylidene}acetic acid melting at 250° C. is obtained.

Ethyl (E)-(RS)-2-{3,4-dihydro-6-[3-(2,3-dihydro-1-methyl-2-oxo-5-phenyl-1H-1,4-benzo[f]diazepin-3-yl)ureido]-4-2H-benzopyranylidene}acetate can be prepared in the following manner: a solution of 2.1 g of ethyl (E)-2-(3,4-dihydro-6-isocyanato-4-2H-benzopyranylidene)acetate in 20 cm³ of tetrahydrofuran is added in the course of 10 minutes to a solution of 2 g of (RS)-3-amino-1-methyl-2-oxo-5-phenyl-1,4-benzo[f]diazepine in 25 cm³ of tetrahydrofuran. After stirring for 1 hour at a temperature near to 20° C., the reaction mixture is concentrated under reduced pressure (2.7 kPa) and taken up in 50 cm³ of ethyl acetate. The organic phase is washed with 50 cm³ of water, dried over magnesium sulphate and then evaporated to dryness to give 3.4 g of product in the form of an ochre solid foam. By crystallization in 40 cm³ of ethyl acetate, 2.4 g of ethyl (E)-(RS)-2-{3,4-dihydro-6-[3-(2,3-dihydro-1-methyl-2-oxo-5-phenyl-1H-1,4-benzo[f]diazepin-3-yl)ureido]-4-2H-benzopyranylidene}acetate melting at 230° C. are obtained.

Ethyl (E)-2-(3,4-dihydro-6-isocyanato-4-2H-benzopyranylidene)acetate can be obtained in the following manner: a solution of 1.52 g of bis(trichloromethyl) carbonate in 20 cm³ of toluene is added in the course of 10 minutes to a suspension of 2.4 g of ethyl (E)-2-(6-amino-3,4-dihydro-4-2H-benzopyranylidene)acetate and 0.1 g of animal charcoal in 45 cm³ of toluene, cooled to a temperature near to –20° C. After stirring for 10 minutes at a temperature near to –20° C., the mixture is brought for 1 hour to a temperature near to 110° C. before cooling to a temperature near to 20° C. It is filtered on Celite and the filtrate is concentrated to dryness under reduced pressure (2.7 kPa) to obtain 2.7 g of (E)-2-(3,4-dihydro-6-isocyanato-4-2H-benzopyranylidene)acetate in the form of an oil which is used as such in the subsequent syntheses.

Ethyl (E)-2-(6-amino-3,4-dihydro-4-2H-benzopyranylidene)acetate can be prepared in the following manner: 2.7 cm³ of a 12N aqueous solution of hydrochloric acid are added to a suspension of 3.4 g of ethyl (E)-2-(6-nitro-3,4- dihydro-4-2H-benzopyranylidene)acetate and 2.7 g of iron powder in 90 cm³ of 50% aqueous ethanol. The mixture is heated to a temperature near to 80° C. for 1 hour and then cooled to a temperature near to 50° C. The mixture is filtered on Celite and washed with 20 cm³ of ethanol and then 20 cm³ of water and then evaporated under reduced pressure (2.7 kPa). The residue is acidified to pH 1 with 25 cm³ of an N solution of hydrochloric acid and washed with 100 cm³ of diethyl ether. The aqueous phase is rendered alkaline to pH 8 with sodium hydrogencarbonate and extracted with 200 cm³ of ethyl acetate. The extract is dried over magnesium sulphate and the filtrate is evaporated to obtain 2.5 g of ethyl (E)-2-(6-amino-3,4-dihydro-4-2H-benzopyranylidene)acetate melting at 97° C.

Ethyl (E)-2-(6-nitro-3,4-dihydro-4-2H-benzopyranylidene)acetate can be obtained in the following manner: 9.9 g of a 60% suspension of sodium hydride in oil are introduced into an apparatus purged with nitrogen. The oil is removed by two washings with 100 cm³ of hexane. 200 cm³ of tetrahydrofuran are added and then, at a temperature near to 20° C., 62 cm³ of triethyl phosphonoacetate are run in in the course of 30 minutes. After stirring for 10 minutes at a temperature near to 20° C., 12 g of 3,4-dihydro-6-nitro-4-one 2H-benzopyran are run in. After stirring for 1 hour at room temperature near to 20° C., the reaction mixture is concentrated under reduced pressure (2.7 kPa), diluted with 500 cm³ of water and extracted with two times 200 cm³ of ethyl acetate. The organic phases are combined and washed with 500 cm³ of water, dried over magnesium sulphate and evaporated to dryness to give an oil which is chromatographed on a column of diameter 6 cm containing 800 cm³ of silica, eluting with a cyclohexane/ethyl acetate mixture (93:7 by volume) and collecting fractions of 200 cm³. The fractions between 1 and 2.2 liters are collected and evaporated to dryness to give 3.5 g of ethyl (E)-2-(6-nitro-3,4-dihydro-4-2H-benzopyranylidene)acetate melting at 135° C.

3,4-Dihydro-6-nitro-4-2H-benzopyranone can be obtained by the method described by C. D. HURD and S. HAYAO, J. Amer. Chem. Soc., 76, 5065 (1954).

EXAMPLE 8

A solution of 3.5 g of tert-butyl (E)-(RS)-3-{3-[2,3-dihydro-2-oxo-5-phenyl-1-(1-pyrrolidinyl)carbonylmethyl-1H-1,4-benzo[f]diazepin-3-yl]ureido}-2-phenylmethyleneaminooxyacetate in 15 cm³ of trifluoroacetic acid is stirred for 2 hours at a temperature near to 20° C. The reaction mixture is concentrated under reduced pressure (2.7 kPa). The residue is taken up in 50 cm³ of water and the solution is extracted with 50 cm³ of ethyl acetate. The organic phase is dried over magnesium sulphate and evaporated to dryness to obtain 3 g of yellow oil. By crystallisation in 40 cm³ of isopropyl acetate, 1.6 g of (E)-(RS)-3-{3-[2,3-dihydro-2-oxo-5-phenyl-1-(1-pyrrolidinyl)carbonylmethyl-1H-1,4-benzo[f]diazepin-3-yl]ureido}-2-phenylmethyleneaminooxyacetic acid melting at 175° C. are obtained.

tert-Butyl (E)-(RS)-3-{3-[2,3-dihydro-2-oxo-5-phenyl-1-(1-pyrrolidinyl)carbonylmethyl-1H-1,4-benzo[f]diazepin-3-yl]ureido}-2-phenylmethyleneaminooxyacetate can be obtained in the following manner: a solution of 2.35 g of tert-butyl (E)-3-isocyanatophenylmethyleneaminooxyacetate in 25 cm³ of tetrahydrofuran is added in the course of 10 minutes to a solution of 2.8 g of (RS)-3-amino-2,3-dihydro-2-oxo-5-phenyl-1-(1-pyrrolidinyl)carbonylmethyl-1H-1,4-benzo[f]diazepine in 30 cm³ of tetrahydrofuran and kept for 1 hour at a temperature near to 20° C. The reaction mixture is evaporated to dryness under reduced pressure (2.7 kPa). The residue is purified by chromatography on a column of diameter 4 cm containing 400 cm³ of silica, eluting first with 500 cm³ of ethyl acetate/cyclohexane mixture (40:60 by volume) and then with 500 cm³ of ethyl acetate/cyclohexane mixture (50:50 by volume) and then with 1 liters of ethyl acetate/cyclohexane mixture (60:40 by volume) and then with 500 cm³ of ethyl acetate/cyclohexane mixture (80:20 by volume) and then with pure ethyl acetate and collecting fractions of 200 cm³. The fractions between 2.2 and 3 liters are combined and evaporated to dryness to give 3.5 g of tert-butyl (E)-(RS)-3-{3-[2,3-dihydro-2-oxo-5-phenyl-1-(1-pyrrolidinyl)carbonylmethyl-1H-1,4-benzo[f]diazepin-3-yl]ureido}-2-phenylmethyleneaminooxyacetate in the form of a solid foam which is used as such in the subsequent syntheses.

tert-Butyl (E)-3-isocyanatophenyl-methyleneaminooxyacetate can be obtained in the following manner: 0.6 g of animal charcoal is added to a solution of 6.2 g of tert-butyl (E)-3-phenylmethyleaminooxy acetate in 100 cm³ of toluene, this suspension is cooled to a temperature near to −30° C., and then 3 cm³ of trichloromethyl chloroformate in 5 cm³ of toluene are added in the course of 10 minutes and the mixture is allowed to warm to a temperature near to 20° C. before heating for 2 hours at a temperature near to 110° C. The mixture is cooled to a temperature near to 20° C. and filtered on Celite. The precipitate is washed with 25 cm³ of toluene and the toluene phases are combined and concentrated to dryness (2.7 kPa). 6.8 g of tert-butyl (E)-3-isocyanatophenylmethyleneaminooxyacetate are thus obtained in the form of an oil which is used as such in the subsequent syntheses.

tert-Butyl (E)-3-aminophenylmethyleneaminooxyacetate can be obtained in the following manner: 0.75 of platinum dioxide is added to a solution of 7.5 g of tert-butyl (E)-3-phenylmethyleneaminooxyacetate in 100 cm³ of ethanol. The suspension is stirred for 45 minutes at a temperature near to 20° C. under a hydrogen atmosphere (128 kPa). The catalyst is separated by filtration and the filtrate is concentrated under reduced pressure (2.7 kPa). The residue is taken up in 50 cm³ of water and extracted with 50 cm³ of ethyl acetate. After drying over magnesium sulphate, the filtrate is evaporated to dryness to obtain 6.2 g of tert-butyl (E)-3-aminophenylmethyleneaminooxyacetate in the form of an oil which is used as such in the subsequent syntheses.

tert-Butyl (E)-3-phenylmethyleneaminooxyacetate can be obtained in the following manner: working under an argon atmosphere, 1.3 g of a 60% dispersion of sodium hydride in oil are washed with two times 50 cm³ of hexane. 100 cm³ of tetrahydrofuran are added and then the mixture is cooled to a temperature near to 5° C. A solution of 4.98 g of (E)-3-nitrobenzaldoxime in 20 cm³ of tetrahydrofuran is added in the course of 15 minutes and the mixture is stirred for 1 hour at a temperature near to 20° C. 5 cm³ of tert-butyl 2-bromoacetate are then run in in the course of 15 minutes and the mixture is stirred at a temperature near to 25° C. 200 cm³ of water and 100 cm³ of ethyl acetate are run in. The organic phase is decanted and washed with 100 cm³ of water. The organic phases are dried over magnesium sulphate and the filtrate is concentrated to dryness (2.7 kPa) to obtain tert-butyl (E)-3-nitrophenylmethyleneaminooxyacetate melting at 110° C.

(E)-3-Nitrobenzaldoxime can be prepared by the method described by S. GABRIEL, Ber., 16, 1997 (1883).

EXAMPLE 9

A suspension of 1.3 g of a mixture of Z and E isomers (50:50) of (RS)-{1-{3-{3-[2,3-dihydro-2-oxo-5-phenyl-1-

(1-pyrrolidinyl)carbonylmethyl-1H-1,4-benzo[f]diazepin-3-yl]ureido}phenyl}-1-ethoxycarbonylmethylene}-2-aminooxyacetic acid in 15 cm³ of ethanol, 3.8 cm³ of 1N sodium hydroxide and 5 cm³ of water is stirred for 16 hours at a temperature near to 20° C. The reaction mixture is concentrated under reduced pressure (2.7 kPa) and diluted with 50 cm³ of water. The aqueous phase is washed with 30 cm³ of diethyl ether and then acidified to pH 1 with 5 cm³ of a 1N aqueous solution of hydrochloric acid. The aqueous phase is extracted with 50 cm³ of ethyl acetate, dried over magnesium sulphate and concentrated under reduced pressure to a volume of 10 cm³ before diluting with 40 cm³ of diisopropyl ether. By filtration, 0.63 g of a mixture of Z and E isomers (50:50) of (RS)-2-{3-{3-[2,3-dihydro-2-oxo-5-phenyl-1-(1-pyrrolidinyl)carbonylmethyl-1H-1,4-benzo[f]diazepin-3-yl]ureido}phenyl}-2-(carboxymethyloxyimino)acetic acid melting at 190° C. is obtained.

The mixture of Z and E isomers (50:50) of (RS)-{1-{3-{3-[2,3-dihydro-2-oxo-5-phenyl-1-(1-pyrrolidinyl)carbonylmethyl-1H-1,4-benzo[f]diazepin-3-yl]ureido}phenyl}-1-ethoxycarbonylmethylene}-2-aminooxyacetic acid can be obtained in the following manner: a solution of 1.45 g of a mixture of Z and E isomers (50:50) of ethyl (RS)-2-{3-{3-[2,3-dihydro-2-oxo-5-phenyl-1-(1-pyrrolidinyl)carbonylmethyl-1H-1,4-benzo[f]diazepin-3-yl]ureido}phenyl}-2-(tert-butoxycarbonylmethoxyimino)acetate in 30 cm³ of trifluoroacetic acid is stirred for 2 hours at a temperature near to 20° C. The reaction mixture is concentrated under reduced pressure (2.7 kPa). The residue is taken up in 50 cm³ of diisopropyl ether to give 1.35 g of a white solid. This solid is dissolved in the presence of 1 g of sodium hydrogencarbonate in 50 cm³ of water and the organic phase is rapidly washed with 50 cm³ of ethyl acetate. The aqueous phase is acidified to pH=1 with a 1N aqueous solution of hydrochloric acid. By extraction with 100 cm³ of ethyl acetate, drying over magnesium sulphate and concentration to dryness, 1.3 g of a mixture of Z and E isomers (50:50) of (RS) -{1-{3-{3-[2,3-dihydro-2-oxo-5-phenyl-1-(1-pyrrolidinyl)carbonylmethyl-1H-1,4-benzo[f]diazepin-3-yl]ureido}phenyl}-1-ethoxycarbonylmethylene}-2-aminooxyacetic acid melting at about 150° C. are obtained.

The mixture of Z and E isomers (50:50) of ethyl (RS)-2-{3-{3-[2,3-dihydro-2-oxo-5-phenyl-1-(1-pyrrolidinyl)carbonylmethyl-1H-1,4-benzo[f]diazepin-3-yl]ureido}phenyl}-2-(tert-butoxycarbonylmethoxyimino)acetate can be obtained in the following manner: 1.55 g of a mixture of Z and E isomers of ethyl 3-isocyanato-alpha-tert-butoxycarbonylmethoxyiminophenylacetate in 10 cm³ of tetrahydrofuran are added in the course of 5 minutes to a solution of 1.45 g of 3-amino-2,3-dihydro-2-oxo-5-phenyl-1-(1-pyrrolidinyl)carbonylmethyl-1H-1,4-benzo[f]diazepine in 20 cm³ of tetrahydrofuran and the mixture is stirred for 3 hours at a temperature near to 20° C. The mixture is poured onto 50 cm³ of water and extracted with 100 cm³ of ethyl acetate. The extract is dried over magnesium sulphate and concentrated under reduced pressure (2.7 kPa). The residue (2.2 g) is purified by chromatography on a column of diameter 3.5 cm containing 200 cm³ of silica, eluting with a dichloromethane/methanol mixture (97:3 by volume) and collecting fractions of 50 cm³. The fractions between 250 and 400 cm³ are combined and evaporated to dryness to give 1.45 g of a mixture of Z and E isomers (50:50) of ethyl (RS)-2-{3-{3-[2,3-dihydro-2-oxo-5-phenyl-1-(1-pyrrolidinyl)carbonylmethyl-1H-1,4-benzo[f]diazepin-3-yl]ureido}phenyl}-2-(tert-butoxycarbonylmethoxyimino)acetate in the form of a solid foam which is used as such in the subsequent syntheses.

The mixture of Z and E isomers of ethyl 3-isocyanato-alpha-tert-butoxycarbonylmethoxyiminophenylacetate can be obtained in the following manner: a solution of 0.67 g of bis(trichloromethyl) carbonate in 15 cm³ of dry toluene is added in the course of 10 minutes to a suspension of 1.4 g of ethyl (Z)-3-amino-alpha-tert-butoxycarbonylmethoxyiminophenylacetate and 0.05 g of animal charcoal in 30 cm³ of dry toluene cooled to a temperature near to −20° C. The mixture is allowed to warm to a temperature near to 20° C. and is then brought for 1 hour to a temperature near to 110° C. The mixture is cooled to a temperature near to 20° C. and filtered on Celite, and the filtrate is washed with 5 cm³ of dry toluene and concentrated to dryness under reduced pressure (1.2 kPa) to obtain 1.55 g of a mixture of Z and E isomers of ethyl 3-isocyanato-alpha-tert-butoxycarbonylmethoxyiminophenylacetate in the form of an oil which is used as such in the subsequent syntheses.

Ethyl (Z)-3-amino-alpha-tert-butoxycarbonylmethoxyiminophenylacetate can be obtained in the following manner: 0.15 g of platinum dioxide is added to a solution of 2.61 g of ethyl (Z)-3-nitro-alpha-tert-butoxycarbonylmethoxyiminophenylacetate in 70 cm³ of ethanol. The suspension is stirred for 40 minutes at a temperature near to 20° C. under a hydrogen atmosphere (128 kPa). The catalyst is separated by filtration and the filtrate is concentrated to dryness under reduced pressure (2.7 kPa) to give 2.3 g of ethyl (Z)-3-amino-alpha-tert-butoxycarbonylmethoxyiminophenylacetate in the form of an oil which is used as such in the subsequent syntheses.

Ethyl (Z)-3-nitro-alpha-tert-butoxycarbonylmethoxy-iminophenylacetate can be obtained in the following manner: 0.46 g of a 60% dispersion of sodium hydride in oil is introduced into an apparatus purged with argon. The oil is removed by two washings with 40 cm³ of heptane. 30 cm³ of tetrahydrofuran are added, and then 2.5 g of ethyl (Z)-3-nitro-alpha-hydroxyiminophenylacetate in the course of 15 minutes at a temperature near to 20° C. After 10 minutes, 1.8 cm³ of tert-butyl 2-bromoacetate in 10 cm³ of tetrahydrofuran are added in the course of 10 minutes. After stirring for 1 hour at a temperature near to 20° C., the mixture is diluted with 100 cm³ of ethyl acetate and washed with 100 and then 50 cm³ of water, dried over magnesium sulphate, filtered and concentrated to dryness under reduced pressure (2.7 kpa) to obtain 3 g of ethyl (Z)-3-nitro-alpha-tert-butoxycarbonylmethoxyiminophenylacetate in the form of an oil which is used as such in the subsequent syntheses.

Ethyl (Z)-3-nitro-alpha-hydroxyiminophenylacetate can be obtained in the following manner: a solution of 62 g of hydroxylamine hydrochloride in 200 cm³ of water is added to a solution of 10 g of ethyl 3-nitrophenyl-glyoxylate in 250 cm³ of pyridine and the mixture is brought for 2 hours to a temperature near to 100° C. The reaction mixture is concentrated under reduced pressure (1.2 kPa). The residue is diluted with 250 cm³ of water and extracted with 250 cm³ of ethyl acetate. The organic phase is washed with a 1N aqeuous solution of hydrochloric acid, dried over magnesium sulphate, filtered and evaporated to dryness to give a white solid. This solid is purified by chromatography on a column of diameter 4 cm containing 500 cm³ of silica, eluting with a cyclohexane/ethyl acetate mixture and collecting fractions of 100 cm³. The fractions between 1 and 1.2 liters are combined and concentrated to dryness to give 1.8 g of ethyl (E)-3-nitro-alpha-hydroxyiminophenylacetate in the form of a colorless oil; the fractions between 1.4 and 1.6 liters are combined and concentrated to dryness to give 2.5 g of ethyl (Z)-3-nitro-alpha-hydroxyiminophenylacetate in the form of a solid which is used as such in the subsequent syntheses.

Ethyl 3-nitrophenylglyoxylate can be prepared by the method described by E. ADLEROVA, P. VEJDELKOVA and M. PROTIVA, Collection Czech. Chem. Commun., 29, 97–120 (1964).

EXAMPLE 10

A solution of 2 g of (RS)-2,3-dihydro-3-isocyanato-2-oxo-5-phenyl-1-(1-pyrrolidinyl)carbonylmethyl-1H-1,4-benzo[f]diazepine in 15 cm³ of dry tetrahydrofuran is added in the course of 10 minutes to a solution of 1.1 g of 5-(3-aminobenzyl)-2,2-dimethyl-1,3-dioxane-4,6-dione in 20 cm³ of dry tetrahydrofuran. After stirring for 1 hour at a temperature near to 20° C., 100 cm³ of ethyl acetate are run in and the organic phase is extracted with 50 cm³ of water and then 35 cm³ of a 5% aqueous solution of sodium hydrogencarbonate. The aqueous phases are combined and acidified to pH 1 with a 2N aqueous solution of hydrochloric acid and then extracted with 100 cm³ of ethyl acetate. The organic phase is dried over magnesium sulphate, filtered and evaporated to dryness under reduced pressure (2.7 kPa). The residue is purified by chromatography under pressure (4.1 MPa) on a column containing 300 g of 55–105 micron silica, eluting with a dichloromethane/methanol mixture (97:3) by volume. The fractions between 1850 and 2500 cm³ are combined and evaporated to dryness (2.7 kPa) to give 1.3 g of a residue which is taken up in 30 cm³ of diethyl ether. 1 g of (RS)-5-{3-{3-[2,3-dihydro-2-oxo-5-phenyl-1-(1-pyrrolidinyl)carbonylmethyl-1H-1,4-benzo[f]diazepin-3-yl]ureido}benzyl}-2,2-dimethyl-1,3-dioxane-4,6-dione melting at 190° C. is thus obtained.

(RS)-2,3-Dihydro-3-isocyanato-2-oxo-5-phenyl-1-(1-pyrrolidinyl)carbonylmethyl-1H-1,4-benzo[f]diazepine can be obtained in the following manner: a solution of 0.82 g of bis(trichloromethyl) carbonate in 15 cm³ of toluene is added in the course of 15 minutes to a suspension of 2 g of (RS)-3-amino-2,3-dihydro-2-oxo-5-phenyl-1-(1-pyrrolidinyl)carbonylmethyl-1H-1,4-benzo[f]diazepine and 0.03 g of animal charcoal in 30 cm³ of dry toluene cooled to a temperature near to −30° C. After stirring for 15 minutes at a temperature near to −30° C., the mixture is allowed to return to a temperature near to 20° C. and then brought to a temperature near to 110° C. for 40 minutes. After cooling to a temperature near to 20° C., the mixture is filtered on Celite, rinsed with 5 cm³ of dry toluene and concentrated under reduced pressure (1.2 kPa) to obtain 2.1 g of (RS)-2,3-dihydro-3-isocyanato-2-oxo-5-phenyl-1-(1-pyrrolidinyl)carbonylmethyl-1H-1,4-benzo[f]diazepine in the form of a solid foam which is used as such in the subsequent syntheses.

5-(3-Aminobenzyl)-2,2-dimethyl-1,3-dioxane-4,6-dione can be obtained in the following manner: a suspension of 7 g of 5-(3-nitrobenzylidene)-2,2-dimethyl-1,3-dioxane-4,6-dione and 0.2 g of 10% palladium on carbon in 300 cm³ of ethanol is stirred for 40 minutes at a temperature near to 20° C. under a hydrogen atmosphere (128 kPa). The catalyst is separated by filtration and the filtrate is concentrated to dryness under reduced pressure (2.7 kPa) to give 6.4 g of residue. This residue is purified by chromatography on a column of diameter 4 cm containing 200 cm² of silica, eluting with an ethyl acetate/cyclohexane mixture (60:40 by volume) and collecting fractions of 60 cm³. The fractions between 180 and 360 cm³ are combined and concentrated to dryness to give 3.2 g of an oil which is again purified by chromatography under pressure (2.1 MPa) on a column containing 300 g of 55–105 micron silica, eluting with a cyclohexane/ethyl acetate mixture (60:40 by volume). The fractions between 1850 and 2550 cm³ are combined and evaporated to dryness (2.7 kPa) to give 1.3 g of 5-(3-aminobenzyl)-2,2-dimethyl-1,3-dioxane-4,6-dione in the form of an oil which is used as such in the subsequent syntheses.

5-(3-Nitrobenzylidene)-2,2-dimethyl-1,3-dioxane-4,6-dione can be obtained in the following manner: a solution of 30.2 g of 3-nitrobenzaldehyde and 2,2-dimethyl-1,3-dioxane-4,6-dione in 400 cm³ of dimethylformamide is stirred for 18 hours at a temperature near to 20° C. The reaction mixture is diluted with 500 cm³ of ethyl acetate, washed five times with water, dried over magnesium sulphate, filtered and concentrated to dryness (1.2 kPa) to give an oil. This oil is crystallized in 100 cm³ of ethanol to give 26 g of 5-(3-nitrobenzylidene)-2,2-dimethyl-1,3-dioxane-4,6-dione in the form of a solid melting at 128° C.

EXAMPLE 11

A solution of 1.3 g of tetrabutylammonium (E)-2-(3-aminophenyl)ethylenesulphonate in 30 cm³ of dichloromethane is added in the course of 5 minutes to a solution of (RS)-1-(N,N-diethylcarbamoylmethyl)-2,3-dihydro-3-isocyanato-2-oxo-5-phenyl-1H-1,4-benzo[f]diazepine and 0.05 g of N,N-4-dimethylaminopyridine for 18 hours at a temperature near to 20° C., the mixture is heated for 2 hours 30 minutes to a temperature near to 60° C. The reaction mixture is concentrated under reduced pressure (2.7 kPa). The residue is chromatographed on a column of diameter 3 cm containing 200 cm³ of silica eluting with a dichloromethane/ethanol mixture (100:0, then 95:5, then 90:10, then 80:20 by volume). The fractions containing the expected product are combined and evaporated to dryness under reduced pressure to give 1.37 g of tetrabutylammonium (E)-(RS)-2-{3-{3-[1-(N,N-diethylcarbamoylmethyl)-2,3-dihydro-2-oxo-5-phenyl-1H-1,4-benzo[f]diazepin-3-yl]ureido}phenyl}ethylenesulphonate in the form of a brown solid foam. This tetrabutylammonium salt is stirred in the presence of 10 g of sulphonic acid resin (IRN-77) in 50 cm³ of methanol, for 16 hours, at a temperature near to 20° C. The resin is filtered and washed with three times 20 cm³ of methanol. The filtrate is stirred in the presence of 0.25 of animal charcoal, filtered and evaporated to dryness under reduced pressure (2.7 kPa). The residue is dissolved in 5 cm³ of methanol, diluted with 40 cm³ of ethanol and then cooled for 16 hours at a temperature of +5° C. 0.22 g of a solid is thus removed. The filtrate is diluted with 50 cm³ of ethyl ether to obtain 0.31 g of (E)-(RS)-2-{3-{3-[1-(N,N-diethylcarbamoylmethyl)-2,3-dihydro-2-oxo-5-phenyl-1H-1,4-benzo[f]diazepin-3-yl]ureido}phenyl}ethylenesulphonic acid melting at 250° C. with decomposition.

(RS)-1-(N,N-Diethylcarbamoylmethyl)-2,3-dihydro-3-isocyanato-2-oxo-5-phenyl-1H-1,4-benzo[f]diazepine can be obtained as in Example 10 for the preparation of (RS)-2,3-dihydro-3-isocyanato-2-oxo-5-phenyl-1-(1-pyrrolidinyl)carbonylmethyl-1H-1,4-benzo[f]diazepine, but starting from 1.6 g of (RS)-1-(N,N-diethylcarbamoylmethyl)-2,3-dihydro-2-oxo-5-phenyl-1H-1,4-benzo[f]diazepine, 0.89 g of bis(trichloromethyl)-carbamate and 0.1 g of animal charcoal in 25 cm³ of toluene. 1.71 g of (RS)-1-(N,N-diethylcarbamoylmethyl)-2,3-dihydro-3-isocyanato-2-oxo-5-phenyl-1H-1,4-benzo[f]diazepine can thus be obtained in the form of a solid foam which is used as such in the subsequent syntheses.

Tetrabutylammonium (E)-2-(3-aminophenyl)ethylenesulphonate can be obtained in the following manner: a solution of tetrabutylammonium (E)-2-(3-nitrophenyl)ethylenesulphonate in 30 cm³ of water and 30 cm³ of a 20% solution of ammonium sulphide is stirred for 21 hours at a temperature near to 20° C., then heated for 2 hours 30 minutes at a temperature near to 60° C. and then heated for 3.5 hours at a temperature near to 80° C. The reaction mixture is concentrated to dryness under reduced pressure (1.2 kPa) and the residue is taken up in 60 cm³ of water, filtered and washed with two times 20 cm³ of water to eliminate an insoluble brown material. The filtrate is extracted with 7 times 100 cm³ of dichloromethane. 10 g of sodium dihydrogenphosphate is added, and the mixture is then reextracted with 3 times 100 cm³ of dichloromethane. The chloromethylene phases are combined, dried over magnesium sulphate and concentrated to dryness to give 4.48 g of tetrabutylammonium (E)-2-(3-aminophenyl)-ethylenesulphonate in the form of an oil which is used as such in the subsequent syntheses.

Tetrabutylammonium (E)-2-(3-nitrophenyl)ethylenesulphonate can be obtained in the following manner: a suspension of 13.08 g of ethyl (E)-2-(3-nitrophenyl)ethylenesulphonate in 25 cm³ of 95% sulphuric acid and 4 cm³ of water is brought in the course of 5.5 hours to a temperature near to 60° C. The reaction mixture is cooled to a temperature near to 20° C., poured onto 225 cm³ of water and washed with 100 cm³ of diethyl ether. The organic phase is washed with 50 cm³ of water. The aqueous phases are treated with 16.35 g of tetrabutylammonium hydrogensulphate and extracted with 200 cm³ and then twice with 100 cm³ of dichloromethane. The organic phase is dried over magnesium sulphate, filtered and evaporated to give 22.6 g of tetrabutylammonium (E)-2-(3-nitrophenyl)ethylenesulphonate in the form of an oil which is used as such in the subsequent syntheses.

Ethyl (E)-2-(3-nitrophenyl)ethylenesulphonate can be prepared according to the method described by J. C. CARRETERO, M. DEMILLEQUAND, L. GHOSEZ, Tetrahedron, 43, (21), 5125-34 (1987).

EXAMPLE 12

The reaction is carried out as in Example 11, but starting from 3.2 g of (R,S)-1-(N,N-diethylcarbamoyl-methyl)-2,3-dihydro-3-isocyanato-2-oxo-5-phenyl-1H-1,4-benzo[f]diazepine and 1.2 g of 5-(3-aminobenzyl)-tetrazole in 50 cm³ of tetrahydrofuran. After treatment, 0.4 g of (RS)-5-{3-{3-[1-(N,N-diethylcarbamoylmethyl)-2,3-dihydro-2-oxo-5-phenyl-1H-1,4-benzo[f]diazepin-3-yl]ureido}benzyl}tetrazole melting at 110° C. is obtained.

5-(3-Aminobenzyl)tetrazole can be obtained according to the method described in the Patent WO 91/13907.

EXAMPLE 13

The reaction is carried out as in Example 3, but starting from 1 g of methyl (E)-(RS)-3-{3-[1-(N,N-diethylcarbamoylmethyl)-2,3-dihydro-2-oxo-5-phenyl-1H-1,4-benzo [f]diazepin-3-yl]ureido}-alpha-hydroxyiminophenylacetate and 4.1 cm³ of 1N sodium hydroxide in a mixture of 10 cm³ of ethanol and 4 cm³ of water. After treatment, 0.7 g of (E)-(RS)-3-{3-[1-(N,N diethylcarbamoylmethyl)-2,3-dihydro-2-oxo-5-phenyl-1H-1,4-benzo [f]diazepin-3-yl]ureido}-alpha-hydroxyiminophenylacetic acid is obtained in the form of a solid melting at 230° C.

Methyl (E)-(RS)-3-{3-[1-(N,N-diethylcarbamoylmethyl) -2,3-dihydro-2-oxo-5-phenyl-1H-1,4-benzo [f]diazepin-3-yl]ureido}-alpha-hydroxyiminophenylacetate can be obtained in the following manner: the reaction is carried out as in Example 12, but starting from 3.5 g of (RS)-1-(N,N-diethylcarbamoylmethyl)-2,3-dihydro-3-isocyanato-2-oxo-5-phenyl-1H-1,4-benzo [f]diazepine and 1.5 g of methyl (E)-3-amino-alpha-hydroxyiminophenylacetate in 30 cm³ of tetrahydrofuran. After treatment, 2.9 g of methyl (E)-(RS)-3-{3-[1-(N,N-diethylcarbamoylmethyl)-2,3-dihydro-2-oxo-5-phenyl-1H-1,4-benzo [f]diazepin-3-yl]ureido}-alpha-hydroxyiminophenylacetate are obtained in the form of a solid which is used as such in the subsequent syntheses.

Methyl (E)-3-amino-alpha-hydroxyiminophenylacetate can be obtained in the following manner: the reaction is carried out as in Example 9 for the preparation of ethyl (Z)-3-amino-alpha-tert-butoxycarbonylmethoxyimino-phenylacetate, but starting from 3.4 g of methyl (E)-3-nitro-alpha-hydroxyiminophenylacetate and 0.034 g of platinum dioxide in 20 cm³ of methanol. After treatment, 2.9 g of methyl (E)-3-amino-alpha-hydroxyiminophenylacetate are obtained in the form of a solid which is used as such in the subsequent syntheses.

Methyl (E)-3-nitro-alpha-hydroxyiminophenylacetate can be obtained as in Example 9 for the preparation of ethyl (E)-3-nitro-alpha-hydroxyiminophenylacetate, but starting from 15 g of methyl 3-nitrophenylglyoxylate and 10 g of hydroxylamine hydrochloride in a mixture of 250 cm³ of pyridine and 30 cm³ of water, for 30 minutes at 70° C. After treatment, 3.4 g of methyl (E)-3-nitro-alpha-hydroxyiminophenylacetate melting at 140° C. and 6.1 g of methyl (Z)-3-nitro-alpha-hydroxyiminophenylacetate melting at 190° C. are obtained.

Methyl 3-nitrophenylglyoxylate can be prepared according to the method described by E. ADLEROVA, P. VEJDELKOVA, M. PROTIVA, Collection Czech. Chem. Commun., 29, 97–120 (1964).

EXAMPLE 14

The reaction is carried out as in Example 5, but starting from 0.6 g of tert-butyl (RS)-{3-{3-[1-(N,N-diethylcarbamoylmethyl)-2,3-dihydro-5-(2-fluorophenyl)-2-oxo-1H-1, 4benzo [f]diazepin-3-yl]ureido}phenylthio}acetate and 10 cm³ of trifluoroacetic acid. After treatment, 0.39 g of (RS)-{3-{3-[1-(N,N-diethylcarbamoylmethyl)-2,3-dihydro-5-(2-fluorophenyl)-2-oxo-1H-1,4-benzo [f]diazepin-3-yl] ureido}phenylthio}acetic acid melting at 194° C. is obtained.

tert-Butyl (RS)-{3-{3-[1-(N,N-diethylcarbamoyl-methyl)-2,3-dihydro-5-(2-fluorophenyl)-2-oxo-1H-1,4-benzo [f]diazepin-3-yl]ureido}phenylthio}acetate can be obtained as in Example 5 for the preparation of tert-butyl (RS)-{3-{3-[1-(N,N-diethylcarbamoylmethyl)-2,3-dihydro-2-oxo-5-phenyl-1H-1,4-benzo [f]diazepin-3-yl] ureido}phenylthio}acetate, but starting from 0.53 g of tert-butyl (3-isocyanatophenylthio)acetate and 0.7 g of (RS)-1-(N,N-diethylcarbamoylmethyl)-2,3-dihydro-5-(2-fluorophenyl)-2-oxo-1H-1,4-benzo [f]diazepine in 25 cm³ of tetrahydrofuran. After treatment, 0.6 g of tert-butyl (RS)-{3-{3-[1-(N,N-diethylcarbamoylmethyl)-2,3-dihydro-5-(2-fluorophenyl)-2-oxo-1H-1,4-benzo [f]diazepin-3-yl] ureido}phenylthio}acetate is obtained in the form of a solid foam which is used as such in the subsequent syntheses.

(RS)-3-Amino-1-(N,N-diethylcarbamoylmethyl)-2,3-dihydro-5-(2-fluorophenyl)-2-oxo-1H-1,4-benzo [f]diazepine can be obtained as in Example 5 for the preparation of (RS)-3-amino-1-(N,N-diethylcarbamoylmethyl)-2,3-dihydro-2-oxo-5-phenyl-1H-1,4-benzo [f]-diazepine, but starting from 2.5 g of 1-(N,N-diethylcarbamoylmethyl)- 2,3- dihydro-5-(2-fluorophenyl)-3-hydroxyimino-2-oxo-1H-1,4-benzo [f]diazepine and 0.6 g of 5% ruthenium on carbon in 60 cm³ of methanol. After treatment, 0.77 g of (RS)-3-amino-1-(N,N-diethylcarbamoylmethyl)-2,3-dihydro-5-(2-fluorophenyl)-2-oxo-1H-1,4-benzo [f]-diazepine is obtained in the form of a solid foam which is used as such in the subsequent syntheses.

1-(N,N-Diethylcarbamoylmethyl)-2,3-dihydro-5-(2-fluorophenyl)-3-hydroxyimino-2-oxo-1H-1,4-benzo [f]diazepine can be obtained as in Example 5 for the preparation of 1-(N,N-diethylcarbamoylmethyl)-2,3-dihydro-3-hydroxyimino-2-oxo-5-phenyl-1H-1,4-benzo [f]diazepine, but starting from 5.7 g of 1-(N,N-diethylcarbamoylmethyl)-2,3-dihydro-5-(2-fluorophenyl)-1H-1,4-benzo [f]diazepine, 3.47 g of potassium tert-butoxide and 2.3 cm³ of isopentyl nitrite in 200 cm³ of toluene. After treatment, 5.1 g of 1-(N,N-diethylcarbamoylmethyl)-2,3-dihydro-5-(2-fluorophenyl)-3-hydroxyimino-2-oxo-1H-1,4-benzo [f]diazepine melting at 190° C. are obtained.

1-(N,N-Diethylcarbamoylmethyl)-2,3-dihydro-5-(2-fluorophenyl)-2-oxo-1H-1,4-benzo [f]diazepine can be obtained as in Example 5 for the preparation of 1-(N,N-diethylcarbamoylmethyl)-2,3-dihydro-2-oxo-5-phenyl-1H-1,4-benzo [f]diazepine, but starting from 5.08 g of 2,3-dihydro-5-(2-fluorophenyl)-2-oxo-1H-1,4-benzo [f]diazepine, 3.43 g of N,N-diethyl-2-chloroacetamide, 0.33 g of potassium iodide and 8.3 g of potassium carbonate in 60 cm³ of dry dimethylformamide. After treatment, 5.8 g of 1-(N,N-diethylcarbamoylmethyl)-2,3-dihydro-5-(2-fluorophenyl)-2-oxo-1H-1,4-benzo[f]diazepine are obtained in the form of a solid foam which is used as such in the subsequent syntheses.

2,3-Dihydro-5-(2-fluorophenyl)-2-oxo-1H-1,4-benzo[f] diazepine can be prepared according to the method described by L. H. STERNBACH, R. I. FRYER, W. METLESICS, E. REEDER; G. SACH, G. SAUCY and A. STEMPEL, J. Org. Chem., 27, 3788–3796 (1962).

EXAMPLE 15

Working as in Example 1, but starting from 1.4 g of tert-butyl (RS)-{4-{3-[2,3-dihydro-1-(3,3-dimethylpiperidino)carbonylmethyl-2-oxo-5-phenyl-1H-1,4-benzo[f]diazepin-3-yl]ureido}phenylthio}acetate and 5.6 cm³ of trifluoroacetic acid, 0.59 g of (RS)-{4-{3-[2,3-dihydro-1-(3,3-dimethylpiperidino)carbonylmethyl2-oxo-5-phenyl-1H-1,4-benzo[f]diazepin-3-yl]ureido}phenylthio}acetic acid melting at 214° C. is obtained.

tert-Butyl (RS)-{4-{3-[2,3-dihydro-1-(3,3-dimethylpiperidino)carbonylmethyl-2-oxo-5-phenyl-1H-1,4-benzo[f]diazepin-3-yl]ureido}phenylthio}acetate can be prepared in a manner analogous to that described in Example 1 for the preparation of tert-butyl (RS)-{3-{3-[2,3-dihydro-2-oxo-5-phenyl-1-(1pyrrolidinyl)carbonylmethyl-1H-1,4-benzo[f] diazepin -3yl]ureido}phenylthio}acetate, but starting from 1.64 g of (RS)-3-amino-2,3-dihydro-1-(3,3-dimethylpiperidino)carbonylmethyl-2-oxo-5-phenyl-1H-1,4-benzo[f]diazepine and 1.1 g of tert-butyl (4-isocyanatophenylthio)acetate. 1.42 g of tert-butyl (RS)-{4-{3-[2,3-dihydro-1-(3,3-dimethylpiperidino)carbonylmethyl-2-oxo-5-phenyl-1H-1,4-benzo[f]diazepin-3-yl]ureido}phenylthio}acetate are thus obtained in the form of a solid which is used as such in the subsequent syntheses.

tert-Butyl (4-isocyanatophenylthio)acetate can be prepared in a manner analogous to that described in Example 1 for the preparation of tert-butyl (3-isocyanatophenylthio)acetate, but starting from 3.1 g of tert-butyl (4-aminophenylthio)acetate, 1.6 cm³ of trichloromethyl chloroformate and 0.26 g of carbon. 2.3 g of tert-butyl (4-isocyanatophenylthio)acetate are thus obtained in the form of an oil which is used as such in the subsequent syntheses.

tert-Butyl (4-aminophenylthio)acetate can be prepared in a manner analogous to that described in Example 1 for the preparation of tert-butyl (3-aminophenylthio)acetate, but starting from 5 g of 4-aminothiophenol and 7.8 cm³ of tert-butyl bromoacetate. 7.45 g of tert-butyl (4-aminophenylthio)acetate are obtained in the form of an oil which is used as such in the subsequent syntheses.

EXAMPLE 16

Working as in Example 3, but starting from 0.8 g of ethyl (E)-(RS)-{3-{3-[2,3-dihydro-1-(3,3-dimethylpiperidino)carbonylmethyl-2-oxo-5-phenyl-1H-1,4-benzo[f]diazepin-3-yl]ureido}phenyl}-2-propenoate and 1.6 cm³ of a normal aqueous solution of sodium hydroxide, 0.51 g of (E)-(RS)-3-{3-[2,3-dihydro-2-oxo-5-phenyl-1-(3,3-dimethylpiperidino)carbonylmethyl-1H-1,4-benzo[f]diazepin-3-yl]ureido}phenyl}-2-propenoic acid melting at 216° C. is obtained.

(E)-(RS)-{3-{3-[2,3-Dihydro-1-(3,3-dimethylpiperidino)carbonylmethyl-2-oxo-5-phenyl-1H-1,4-benzo[f]diazepin-3-yl]ureido}phenyl}-2-propenoate can be prepared in a manner analogous to that described in Example 3 for the preparation of ethyl (E)-(RS)-3-{3-{3-[1-(N-methyl-N-phenylcarbamoylmethyl)-2-oxo-5-phenyl-2,3-dihydro-1H-1,4-benzo[f]diazepin-3-yl]ureido}phenyl}-2-propenoate, but starting from 1.7 g of (RS)-3-amino-2,3-dihydro-1-(3,3-dimethylpiperidino)carbonylmethyl-2-oxo-5-phenyl-1H-1, 4-benzo[f]diazepine and 0.9 g of ethyl 3-(3-isocyanatophenyl)-2-propenoate. 0.85 g of (E)-(RS)-{3-{3-[2,3-dihydro-1-(3,3-dimethylpiperidino)carbonylmethyl-2-oxo-5-phenyl-1H-1,4-benzo[f]diazepin-3-yl]ureido}phenyl}-2-propenoate is thus obtained in the form of a solid which is used as such in the subsequent syntheses.

EXAMPLE 17

Working as in Example 1, but starting from 2 g of tert-butyl (RS)-{4-{3-[2,3-dihydro-2-oxo-5-phenyl-1-(1-pyrrolidinyl)carbonylmethyl-1H-1,4-benzo[f]diazepin-3-yl]ureido}phenylthio}acetate and 8 cm³ of trifluoro-acetic acid, 1.06 g of (RS)-{4-{3-[2,3-dihydro-2-oxo-5-phenyl-1-(1-pyrrolidinyl)carbonylmethyl-1H-1,4-benzo[f]diazepin-3-yl]ureido}phenylthio}acetic acid melting at 190° C. are obtained.

tert-Butyl (RS)-{4-{3-[2,3-dihydro-2-oxo-5-phenyl-1-(1-pyrrolidinyl)carbonylmethyl-1H-1,4-benzo[f]diazepin-3-yl]ureido}phenylthio}acetate can be prepared in a manner analogous to that described in Example 1 for the preparation of tert-butyl (RS)-{3-{3-[2,3-dihydro-2-oxo-5-phenyl-1-(1-pyrrolidinyl)carbonylmethyl-1H-1,4-benzo[f]diazepin-3-yl]ureido}phenylthio}acetate, but starting from 6.3 g of (RS)-3-amino-2,3-dihydro-2-oxo-5-phenyl-1-(1-pyrrolidinyl)carbonylmethyl-1H-1,4-benzo[f]diazepine and 5.1 g of tert-butyl (4-isocyanatophenylthio)acetate. 2 g of tert-butyl (RS)-{4-{3-[2,3-dihydro-2-oxo-5-phenyl-1-(1-pyrrolidinyl)carbonylmethyl-1H-1,4-benzo[f]diazepin-3-yl]ureido}phenylthio}acetate are thus obtained in the form of a solid which is used as such in the subsequent syntheses.

EXAMPLE 18

Working as in Example 10, but starting from 2 g of (RS)-3-isocyanato-2,3-dihydro-1-methyl-2-oxo-5-phenyl-1H-1,4-benzo[f]diazepine and 2.9 g of tetrabutylammonium (RS)-1-(3-aminophenyl)ethanesulphonate, 1.4 g of a mixture of isomers of potassium (RS)-1-{3-[3-(RS)-2,3-dihydro-2-oxo-5-phenyl-1-methyl- 1H-1,4-benzo[f]diazepin-3-yl)ureido]phenyl}ethanesulphonate melting at 250° C. are obtained.

Tetrabutylammonium (RS)-1-(3-aminophenyl)ethanesulphonate can be prepared as described in Example 2 for the preparation of tetrabutylammonium 3-aminophenylmethanesulphonate, but starting from 21 g of tetrabutylammonium (RS)-1-(3-nitrophenyl)ethanesulphonate and 0.9 g of 5% palladium on carbon in 300 cm³ of ethanol. After treatment, 19 g of tetrabutylammonium (RS)-1-(3-aminophenyl)ethanesulphonate are obtained in the form of an oil which is used as such in the subsequent syntheses.

Tetrabutylammonium (RS)-1-(3-nitrophenyl)ethanesulphonate can be prepared in the following manner: a mixture of 10.4 g of (RS)-3-(1-bromoethyl)nitrobenzene and 8.5 g of sodium hydrogensulphite in 109 cm³ of water is stirred at a temperature near to 70° C. for two hours. After cooling to a temperature near to 20° C., the solution is poured into one liter of an aqueous solution of 89 g of tetrabutylammonium hydrogensulphate and extracted with three times 100 cm³ of dichloromethane. The extracts are combined, washed with 50 cm³ of water, dried over magnesium sulphate and concentrated under reduced pressure. 21 g of tetrabutylammonium (RS)-1-(3-nitrophenyl)ethanesulphonate are thus obtained in the form of an oil which is used as such in the subsequent syntheses.

(RS)-3-(1-Bromoethyl)nitrobenzene can be prepared according to the method described by T. Y. SHEN, N. P. JENSEN, D. H. MINSKER, patent DE 2,331,292.

(RS)-2,3-Dihydro-3-isocyanato-1-methyl-2-oxo-5-phenyl-1H-1,4-benzo[f]diazepine can be prepared in a manner analogous to that described in Example 10 for the preparation of (RS)-2,3-dihydro-3-isocyanato-2-oxo-5-phenyl-1-(1-pyrrolidinyl)carbonylmethyl-1H-1,4-benzo[f]diazepine, but starting from 2 g of (RS)-3-amino-2,3-dihydro-1-methyl-2-oxo-5-phenyl-1H-1,4-benzo[f]diazepine, 0.09 g of carbon and 0.91 cm³ of trichloromethyl chloroformate. 2.13 g of (RS)-2,3-dihydro-3-isocyanato-1-methyl-2-oxo-5-phenyl-1H-1,4-benzo[f]diazepine are thus obtained in the form of an oil which is used as such in the subsequent syntheses.

EXAMPLE 19

Working as in Example 1, but starting from 1 g of tert-butyl (+)-{3-{3-[2,3-dihydro-2-oxo-5-phenyl-1-(1-pyrrolidinyl)carbonylmethyl-1H-1,4-benzo[f]diazepin-3-yl)ureido}phenylthio}acetate and 4 cm³ of trifluoroacetic acid, 0.6 g of (+)-{3-{3-[2,3-dihydro-2-oxo-5-phenyl-1-(1-pyrrolidinyl)carbonylmethyl-1H-1,4-benzo[f]diazepin-3-yl]ureido}phenylthio}acetic acid is obtained whose rotary power is $[\alpha]_D^{20}=+33.7°$ (c=0.994; methanol).

tert-Butyl (+)-{3-{3-[2,3-dihydro-2-oxo-5-phenyl-1-(1-pyrrolidinyl)carbonylmethyl-1H-1,4-benzo[f]diazepin-3-yl)ureido}phenylthio}acetate can be obtained in the following manner: 2 g of tert-butyl (RS)-{3-{3-[2,3-dihydro-2-oxo-5-phenyl-1-(1-pyrrolidinyl)carbonylmethyl-1H-1,4-benzo[f]diazepin-3-yl]ureido}phenylthio}acetate are separated by high performance liquid chromatography on 400 g of support formed of silica coated with cellulose tris(3,5-dimethylphenyl)carbamate prepared according to J. Amer. Chem. Soc., 106, 5357 (1984) and contained in a column of length 23 cm and diameter 6 cm with ethanol as the mobile phase at a rate of 35 cm³/minute, eluting successively:

1 g of tert-butyl (+)-{3-{3-[2,3-dihydro-2-oxo-5-phenyl-1-(1-pyrrolidinyl)carbonylmethyl-1H-1,4-benzo[f]diazepin-3-yl]ureido}phenylthio}acetate whose rotatory power is $[\alpha]_D^{20}=+32.6°$ (c=0.994; methanol), then 0.840 g of a mixture which is recycled under the same conditions to give 0.7 g of tert-butyl (−)-{3-{3-[2,3-dihydro-2-oxo-5-phenyl-1-(1-pyrrolidinyl)carbonylmethyl-1H-1,4-benzo[f]diazepin-3-yl]ureido}phenylthio}acetate whose rotatory power is $[\alpha]_D^{20}=-32.6°$ (c=0.614; methanol).

EXAMPLE 20

Working as in Example 1, but starting from 0.7 g of tert-butyl (−)-{3-{3-[2,3-dihydro-2-oxo-5-phenyl-1-(1-pyrrolidinyl)-carbonylmethyl-1H-1,4-benzo[f]diazepin-3-yl]ureido}-phenylthio}acetate and 3 cm³ of trifluoroacetic acid, 0.4 g of (−)-{3-{3-[2,3-dihydro-2-oxo-5-phenyl-1-(1-pyrrolidinyl)carbonylmethyl-1H-1,4-benzo[f]diazepin-3-yl]ureido}phenylthio}acetic acid whose rotatory power is $[\alpha]_D^{20}=-33.7°$ (c=0.961; methanol) is obtained.

EXAMPLE 21

Working as in Example 1, but starting from 0.4 g of a mixture of isomers of tert-butyl {3-{3-[(RS)-2,3-dihydro-2-oxo-5-phenyl-1-(1-pyrrolidinyl)carbonylmethyl-1H-1,4-benzo[f]diazepin-3-yl]ureido}phenylsulphinyl}acetate and 3 cm³ of trifluoroacetic acid, after recrystallization in isopropanol, 0.138 g of a mixture of isomers of (RS)-{3-{3-[(RS)-2,3-dihydro-2-oxo-5-phenyl-1-(1-pyrrolidinyl)carbonylmethyl-1H-1,4-benzo[f]diazepin-3-yl]ureido}phenylsulphinyl}acetic acid melting at 180° C. is obtained.

The mixture of isomers of tert-butyl (RS)-{3-{[(RS)-2,3-dihydro-2-oxo-5-phenyl-1-(1-pyrrolidinyl)carbonylmethyl-1H-1,4-benzo[f]diazepin-3-yl]ureido}phenylsulphinyl}acetate can be obtained in the following manner: a solution of 3.7 g of Oxone® in 22 cm³ of water is added to a solution of 2 g of tert-butyl (RS)-{3-{3-[2,3-dihydro-2-oxo-5-phenyl-1-(1-pyrrolidinyl)carbonylmethyl-1H-1,4-benzo[f]diazepin-3-yl]ureido}phenylthio}acetate in 16 cm³ of methanol. The suspension is stirred for 16 hours at a temperature near to 20° C. and filtered, and the solid is washed with two times 10 cm³ of water and then ten times 10 cm³ of diethyl ether. By chromatography on silica (eluent: ethyl acetate), the following are eluted successively:

1.05 g of tert-butyl (RS)-{3-{3-[2,3-dihydro-2-oxo-5-phenyl-1-(1-pyrrolidinyl)carbonylmethyl-1H-1,4-benzo[f]diazepin-3-yl]ureido}phenylthio}acetate in the form of a solid which is used as such in the subsequent syntheses, and then 0.4 g of a mixture of isomers of (RS)-{3-{[(RS)-2,3-dihydro-2-oxo-5-phenyl-1-(1-pyrrolidinyl)carbonylmethyl-1H-1,4-benzo[f]diazepin-3-yl]ureido}phenylsulphinyl}acetate in the form of a solid which is used as such in the subsequent syntheses.

EXAMPLE 22

Working as in Example 1, but starting from 1 g of tert-butyl (RS)-{3-{3-[2,3-dihydro-2-oxo-5-phenyl-1-(1-pyrrolidinyl)carbonylmethyl-1H-1,4-benzo[f]diazepin-3-yl]ureido}phenylsulphonyl}acetate and 8 cm³ of trifluoroacetic acid, 0.61 g of (RS)-{3-{3-[2,3-dihydro-2-oxo-5-phenyl-1-(1-pyrrolidinyl)carbonylmethyl-1H-1,4-benzo[f]diazepin-3- yl]ureido}phenylsulphonyl}acetic acid melting at 210° C. is obtained.

EXAMPLE 23

A solution of 0.091 g of lithium hydroxide in 11 cm³ of water is added, at a temperature near to 20° C., to a suspension of 1.4 g of a mixture of isomers of ethyl 2-{3-{3-[2,3-dihydro-2-oxo-5-phenyl-1-(1-pyrrolidinyl)carbonylmethyl-1H-1,4-benzo[f]diazepin-3-yl]ureido}phenylthio}propionate in 140 cm³ of ethanol. The reaction is stirred for 72 hours at a temperature near to 20° C., and then concentrated under reduced pressure. The residue is diluted with 50 cm³ of water and brought to pH 1 with a 1N aqueous solution of hydrochloric acid. The solid which precipitates is filtered, washed with two times 10 cm³ of water and then ten times 10 cm³ of diethyl ether. After recrystallization in methanol and crushing in acetonitrile, 0.64 g of a mixture of isomers of (RS)-2-{3-{3-[(RS)-2,3-dihydro-2-oxo-5-phenyl-1-(1-pyrrolidinyl)carbonylmethyl-1H-1,4-benzo[f]diazepin-3-yl]ureido}phenylthio}propionic acid melting at 184° C. is obtained.

The mixture of isomers of ethyl 2-{3-{3-[2,3-dihydro-2-oxo-5-phenyl-1-(1-pyrrolidinyl)carbonylmethyl-1H-1,4-benzo[f]diazepin-3-yl]ureido}phenylthio}propionate can be obtained in a manner analogous to that described in Example 1 for the preparation of tert-butyl (RS)-{3-{3-[2,3-dihydro-2-oxo-5-phenyl-1-(1-pyrrolidinyl)carbonylmethyl-1H-1,4-benzo[f]diazepin-3-yl]ureido}phenylthio}propionate, but starting from 1.6 g of (RS)-3-amino-2,3-dihydro-2-oxo-5-phenyl-1-(1-pyrrolidinyl)carbonylmethyl-1H-1,4-benzo[f]diazepine and 1.1 g of ethyl 2-(3-isocyanatophenylthio)propionate. 1.7 g of a mixture of isomers of ethyl 2-{3-{3-[2,3-dihydro-2-oxo-5-phenyl-1-(1-pyrrolidinyl)carbonylmethyl-1H-1,4-benzo[f]diazepin-3-yl]ureido}phenylthio}-propionate are thus obtained in the form of a solid which is used as such in the subsequent syntheses.

Ethyl 2-(3-isocyanatophenylthio)propionate can be obtained in a manner analogous to that described in Example 1 for the preparation of tert-butyl (3-isocyanatophenylthio)acetate, but starting for 1 g of ethyl 2-(3-aminophenylthio)propionate, 0.54 cm³ of trichloromethyl chloroformate and 0.09 g of carbon. 1.18 g of ethyl 2-(3-isocyanatophenylthio)propionate are thus obtained in the form of an oil which is used as such in the subsequent syntheses.

Ethyl 2-(3-aminophenylthio)propionate can be prepared in a manner analogous to that described in Example 1 for the preparation of tert-butyl (3-aminophenylthio)acetate, but starting from 9.25 g of 3-aminothiophenol and 18.5 cm³ of ethyl 2-trifluoromethylsulphonyloxypropionate and 10.2 g of potassium carbonate in 200 cm³ of acetonitrile. 4.04 g of ethyl 2-(3-aminophenylthio)propionate are thus obtained in the form of an oil which is used as such in the subsequent syntheses.

Ethyl 2-trifluoromethylsulphonyloxypropionate can be prepared according to the method described by U. BURKARD, F. EFFENBERGER, Chem. Ber., 119, 1594 (1986).

EXAMPLE 24

2.74 g of tert-butyl (RS)-{3-{3-[1-(N,N-diethylcarbamoylmethyl)-2,3-dihydro-2-oxo-5-phenyl-1H-1,4-benzo[f]diazepin-3-yl]ureido}phenylthio}acetate are dissolved slowly in 12 cm³ of trifluoroacetic acid. After stirring for 1 hour at a temperature near to 20° C., 50 cm³ of methanol are added and the mixture is stirred for 18 hours at a temperature near to 20° C. A suspension is obtained which is filtered. The filtrate is evaporated to dryness under reduced pressure (2.7 kPa) to give an oil which is chromatographed on a column of diameter 4 cm containing 600 cm³ of silica, eluting first with 500 cm³ of dichloromethane and then with a dichloromethane/methanol mixture (93:3 by volume) and collecting fractions of 125 cm³. The fractions between 2625 and 3125 cm³ are combined and evaporated to dryness to give 1.4 of solid. By recrystallization in 50 cm³ of aqueous methanol (80:20 by volume), 0.93 g of tert-butyl (RS)-{3-{3-[1-(N,N-diethylcarbamoylmethyl)-2,3-dihydro-2-oxo-5-phenyl-1H-1,4-benzo[f]diazepin-3-yl]ureido}phenylthio}acetate is obtained in the form of a white solid melting at 198° C.

EXAMPLE 25

The reaction is carried out as in Example 11, but starting from 2 g of (RS)-1-(N,N-diethylaminocarbonylmethyl)-2,3-dihydro-3-isocyanato-2-oxo-5-phenyl-1H-1,4-benzo[f]diazepine and 0.92 g of N-{(3-aminophenyl)methyl}acetohydroxamic acid in 40 cm³ of tetrahydrofuran. After treatment, 0.24 g of (RS)-N-{{3-{3-[1-(N,N-diethylaminocarbonylmethyl)-2,3-dihydro-2-oxo-5-phenyl-1H-1,4-benzo[f]diazepin-3-yl]ureido}phenyl}methyl}acetohydroxamic acid is obtained in the form of a white solid melting at 186° C.

N-{(3-Amino-phenyl)methyl}acetohydroxamic acid can be prepared as described in Example 2 for the preparation of tetrabutylammonium 3-aminophenylsulphonate, but starting from 1.92 g of N-{(3-nitrophenyl)methyl}-acetohydroxamic acid and 0.2 g of 10% palladium on carbon in 100 cm³ of methanol. After treatment, 1.73 g of N-{(3-aminophenyl)methyl}acetohydroxamic acid are obtained in the form of an oil which is used as such in the subsequent syntheses.

N-{(3-Nitrophenyl)methyl}acetohydroxamic acid can be obtained in the following manner: 22 cm³ of an 17N aqueous solution of ammonia are added at a temperature near to 25° C. to a solution of 3.55 g of N-acetoxy-N-{(3-nitrophenyl)methyl}acetamide in 120 cm³ of methanol. The reaction mixture is stirred for two hours at a temperature near to 25° C., and then concentrated under reduced pressure. The residue is dissolved in 100 cm³ of a saturated aqueous solution of sodium chloride, dried over magnesium sulphate and concentrated under reduced pressure. 2.46 g of N-{(3-nitrophenyl)methyl}acetohydroxamic acid melting at 80° C. are thus obtained.

N-Acetoxy-N-{(3-nitrophenyl)methyl}acetamide can be obtained in the following manner: a solution of 3.35 g of N-{(3-nitrophenyl)methyl}hydroxylamine in 8 cm³ of acetic anhydride and 80 cm³ of acetic acid is heated to reflux for 3 hours. After cooling to a temperature near to 25° C., the reaction mixture is concentrated under reduced pressure. The residue is dissolved in 100 cm³ of diethyl ether and the organic phase is washed with 50 cm³ of a saturated aqueous solution of sodium chloride, dried over magnesium sulphate and concentrated under reduced pressure. 3.55 g of N-acetoxy-N-{(3-nitrophenyl)methyl}acetamide are thus obtained in the form of an oil which is used as such in the subsequent syntheses.

N-{(3-Nitrophenyl)methyl}hydroxylamine can be obtained in the following manner: 3.78 g of sodium cyanoborohydride are added in portions in the course of two hours at a temperature near to 25° C. to a solution of 5 g of 3-nitrobenzaldoxime in 120 cm³ of acetic acid. The reaction mixture is stirred for 16 hours at a temperature near to 25° C., and then poured into a mixture of 500 cm³ of ethyl acetate and 150 cm³ of a 30% aqueous solution of potassium hydroxide. The organic phase is separated by decantation and the aqueous phase is extracted with three times 500 cm³ of ethyl acetate. The organic phases are combined, dried over magnesium sulphate and concentrated under reduced pressure. The residue is purified by chromatography on 200 cm³ of silica [eluent dichloromethane/methanol (98:2 by volume)]. The fractions containing the expected product are combined and concentrated under reduced pressure. 3.43 g of N-{(3-nitrophenyl)methyl}hydroxylamine are thus obtained in the form of an oil which is used as such in the subsequent syntheses.

The medicaments according to the invention are made up by a compound of formula (I) in free form or in the form of a salt, in the pure state or in the form of a composition in which it is combined with any other pharmaceutically compatible product, which can be inert or physiologically active. The medicaments according to the invention can be employed orally, parenterally, rectally or topically.

Solid compositions for oral administration which can be used are tablets, pills, powders (gelatine capsules, cachets) or granules. In these compositions, the active principle according to the invention is mixed with one or more inert diluents, such as starch, cellulose, sucrose, lactose or silica, under a stream of argon. These compositions can also comprise substances other than the diluents, for example one or more lubricants such as magnesium stearate or talc, a colorant, a coating (coated tablets) or a glaze.

Liquid compositions for oral administration which can be used are solutions, suspensions, emulsions, syrups and pharmaceutically acceptable elixirs containing inert diluents such as water, ethanol, glycerol, vegetable oils or liquid paraffin. These compositions can comprise substances other than the diluents, for example wetting, sweetening, thickening, flavoring or stablizing products.

The sterile compositions for parenteral administration may preferably be aqueous or non-aqueous solutions, or suspensions or emulsions. The solvent or vehicle employed can be water, propylene glycol, polyethylene glycol, vegetable oils, in particular olive oil, injectable organic esters, for example ethyl oleate, or other suitable organic solvents. These compositions can also contain adjuvants, in particular wetting, isotonicizing, emulsifying, dispersing and stabilizing agents. Sterilization can be effected in several ways, for example by sterile filtration, by incorporating sterilizing agents in the composition, by irradiation or by heating. The compositions can also be prepared in the form of sterile solid compositions which can be dissolved at the time of use in sterile water or any other injectble sterile medium.

Compositions for rectal administration are suppositories or rectal capsules which contain, apart from the active product, excipients such as cocoa butter, semi-synthetic glycerides or polyethylene glycols.

Compositions for topical administration may be, for example, creams, lotions, eye lotions, mouthwashes, nasal drops or aerosols.

In human therapy, the compounds according to the invention are particularly useful in the treatment and prevention of disorders connected with CCK and gastrin at the level of the nervous system and the gastrointestinal system. These compounds can thus be used in the treatment and the prevention of psychoses, panic attacks, anxiety disorders, Parkinson's disease, tardive dyskinesia, irritable bowel syndrome, acute pancreatitis, ulcers, disorders of intestinal motility, certain tumors sensitive to CCK, memory disorders, as analgesics, as a potentiator of the analgesic activity of narcotic and non-narcotic analgesic medicaments, in weaning from chronic treatments or drug and alcohol abuse, as an appetite regulator and to control the constriction of the pupil of the eye.

The doses depend on the effect sought after, on the duration of the treatment and on the administration route used; they are generally between 0.05 g and 1 g per day orally for an adult with unit doses ranging from 10 mg to 500 mg of active substance.

Generally, the physician will determine the appropriate dosage as a function of the age, weight and all the other factors peculiar to the subject to be treated.

The following examples illustrate the compositions according to the invention:

EXAMPLE A

According to the usual technique, gelatine capsules filled with 50 mg of active product having the following composition are prepared:

| | |
|---|---|
| (RS)-{3-{3-[2,3-dihydro-2-oxo-5-phenyl-1-(1-pyrrolidinyl)carbonylmethyl-1H-1,4-benzo[f]diazepin-3-yl]ureido}phenylthio}-acetic acid | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

According to the usual technique, tablets filled with 50 mg of active product having the following composition are prepared:

| | |
|---|---|
| (RS)-{3-{3-[2,3-dihydro-2-oxo-5-phenyl-1-(3,3-dimethylpiperidino)carbonylmethyl-1H-1,4-benzo[f]diazepin-3-yl]ureido}phenylthio}-acetic acid | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerol and titanium dioxide (72:3.5:24.5) q.s. 1 245 mg finished film-coated tablet | 245 mg |

EXAMPLE C

An injectable solution containing 10 mg of active product having the following composition id prepared:

| | |
|---|---|
| (E)-(RS)-{3-[1-(N-methyl-N-phenylcarbamoylmethyl)-2-oxo-5-phenyl-2,3-dihydro-1H-1,4-benzo[f]diazepin-3-yl]ureido}-3-phenyl-2-propenoic acid | 10 mg |
| Benzoic acid | 80 mg |
| Benzyl alcohol | 0.06 cm³ |
| Sodium benzoate | 80 mg |
| 95% ethanol | 0.4 cm³ |
| Sodium hydroxide | 24 mg |

| | |
|---|---|
| Propylene glycol | 1.6 cm³ |
| Water q.s. | 4 cm³ |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A compound of formula:

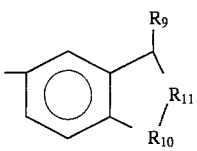

(I)

in which $R_1$ represents a hydrogen or halogen atom or an alkyl, alkoxy, alkylthio, nitro, hydroxyl or cyano radical;

$R_2$ represents an alkyl radical or a —CH($R_5$)—CO—$R_6$ chain in which $R_5$ represents a hydrogen atom or an alkyl, alkoxycarbonyl or phenyl radical which is unsubstituted or substituted by at least one substituent selected from the group consisting of halogen atoms and alkyl, alkoxy, alkylthio and nitro radicals and $R_6$ represents an alkoxy radical, a cycloalkoxy radical which is unsubstituted or substituted by at least one alkyl radical, a cycloalkylalkoxy, phenylalkoxy, polyfluoroalkoxy or cinnamyloxy radical or an —$NR_7R_8$ radical in which $R_7$ and $R_8$, which are identical or different, represent a hydrogen atom, an alkyl radical, a phenyl radical which is unsubstituted or substituted by at least one substituent selected from the group consisting of halogen atoms and alkyl, alkoxy and alkylthio radicals, a cycloalkylalkyl, cycloalkyl, indanyl or phenylalkyl radical or else $R_7$ and $R_8$, together with the nitrogen atom to which they are attached, form a heterocycle selected from the group consisting of piperidino, 1-perhydroazepinyl, 1,2,3,6-tetrahydro-1-pyridyl, 1,2,3,4-tetrahydro-1-quinolyl, 1-pyrrolidinyl, 1,2,3,4-tetrahydro-2-isoquinolyl, morpholino, thiomorpholino and 1-indolyl cyclic systems, these cyclic systems being unsubstituted or substituted by at least one alkyl radical;

$R_3$ represents (a) a phenyl radical substituted by at least one substituent selected from the group consisting of -alk-$SO_3H$, -alk-$PO_3H_2$, —CH=NOH, —CH=NO-alk-COOX, —S-alk-COOX, —$SO_2$-alk-COOX, —CH=CH—COOX, -alk—CO-NHOH, —C(=NOH)—COOX, -alk-N(OH)—CO-alk, -alk-$SO_2H$, —CH=CH—$SO_3H$, —C(=COOX)=N—O—alk—COOX and tetrazolylalkyl radicals or a group of formula:

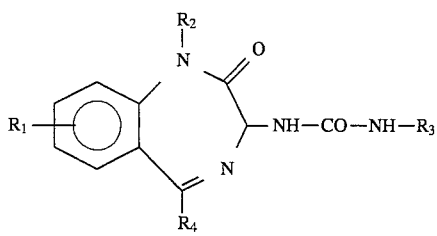

or (b) a cyclic system of formula:

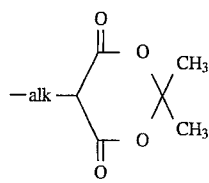

(A)

in which $R_9$ represents an =NOX, =NO-alk-COOX, =CH—COOX, -alk-COOX, -alk-$SO_2H$ or -alk-$SO_3H$ radical, $R_{10}$ represents an oxygen or sulphur atom or a methylene or alkylimino radical and $R_{11}$ represents a methylene or ethylene radical;

$R_4$ represents a pyridyl or phenyl radical unsubstituted or substituted by at least one substituent selected from halogen atoms and alkyl, alkoxy, hydroxyl, carboxyl, and nitro radicals;

alk represents an alkyl or alkylene radical; and

X represents a hydrogen atom or an alkyl radical; it being understood that the alkyl, alkylene and alkoxy radicals and the alkyl, alkylene and alkoxy portions of substituents contain 1 to 4 carbon atoms in a straight or branched chain, and the cycloalkyl radicals and portions of substituents contain 3 to 12 carbon atoms; a pharmaceutically acceptable salt thereof, a racemate thereof, or an enantiomer thereof, when they contain at least one asymmetric center.

2. A compound of formula (I) according to claim 1, wherein $R_1$ represents a hydrogen atom, $R_2$ represents an alkyl radical or -CH($R_5$)$COR_6$ in which $R_5$ represents a hydrogen atom and $R_6$ represents an -$NR_7R_8$ radical in which $R_7$ and $R_8$, together with the nitrogen atom to which they are attached, form a heterocycle selected from the group consisting of piperidino, 1-perhydroazepinyl, 1,2,3,6-tetrahydro-1-pyridyl, 1,2,3,4-tetrahydro-1-quinolyl, 1-pyrrolidinyl, 1,2,3,4-tetrahydro-2-isoquinolyl, morpholino, thiomorpholino and 1-indolyl cyclic systems, these cyclic systems being unsubstituted or substituted by at least one alkyl radical, $R_3$ represents (a) a phenyl radical substituted by at least one substituent selected from the radicals consisting of -alk-$SO_3H$, -alk-$PO_3H_2$, —CH=NOH, —CH=NO-alk-COOX, —S-alk-COOX, —SO-alk-COOX, —$SO_2$-alk-COOX, —CH=CH—COOX, -alk-CO—NHOH, —C(=NOH)-COOX, -alk-N(OH)—CO-alk, -alk-$SO_2H$, —CH=CH—$SO_3H$, —C(COOX)=N—O-alk-COOX, tetrazolylalkyl and a group of formula:

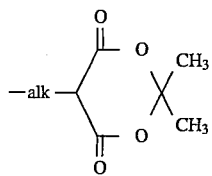

or (b) a cyclic system of formula:

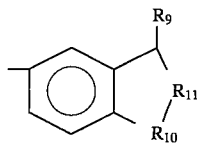

in which $R_9$ represents an =NOX, =NO-alk-COOX, =CH—COOX, -alk-COOX, -alk-SO$_2$H or -alk-SO$_3$H radical, $R_{10}$ represents an oxygen or sulphur atom or a methylene or alkylimino radical and $R_{11}$ represents a methylene or ethylene radical and $R_4$ represents a phenyl radical; a pharmaceutically acceptable salt thereof, a racemate thereof, or an enantiomer thereof, when they contain at least one asymmetric center.

3. A compound of formula (I) according to claim 2, wherein

—NR$_7$R$_8$ represents a 1-pyrrolodinyl or piperidino cyclic system, these cyclic systems being unsubstituted or substituted by at least one alkyl radical; a pharmaceutically acceptable salt thereof, a racemate thereof, or an enantiomer thereof, when they contain at least one asymmetric center.

4. A compound selected from the following compounds:

(RS)-{3-{3-[2,3-dihydro-2-oxo-5-phenyl-1-(1-pyrrolidinyl)carbonylmethyl-1H-1,4-benzo[f]diazepin-3-yl]ureido}phenylthio}acetic acid, (RS)-3-[3-(2,3-dihydro-1-methyl-2-oxo-5-phenyl-1H-1,4-benzo[f]diazepin-3-yl)ureido]phenylmethanesulphonic acid, (RS)-3-{3-[1-(N-methyl-N-phenylcarbamoylmethyl)-2-oxo-5-phenyl-2,3-dihydro-1H-1,4-benzo[f]diazepin-3-yl]-3-phenyl-2(E)propenoic acid, (RS)-{3-{3-[2,3-dihydro-2-oxo-5-phenyl-1-(3,3-dimethylpiperidino)carbonylmethyl-1H-1,4-benzo[f]diazepin-3-yl]ureido}phenylthio}acetic acid, (RS)-{3-{3-[1-(N,N-diethylcarbamoylmethyl)-2,3-dihydro-2-oxo-5-phenyl-1H-1,4-benzo[f]diazepin-3-yl]ureido}phenylthio}acetic acid, (E)-(RS)-N-(2,3-dihydro-1-methyl-2-oxo-5-phenyl-1H-1,4-benzo[f]diazepin-3-yl)-N'-(1-hydroxyimino-6-indanyl)urea, (E)-(RS)-2-{3,4-dihydro-6-[3-(2,3-dihydro-1-methyl-2-oxo-5-phenyl-1H-1,4-benzo[f]diazepin-3-yl)ureido]-4-2H-benzopyranylidene}acetic acid, (E)-(RS)-3-{3-[2,3-dihydro-2-oxo-5-phenyl-1-(1-pyrrolidinyl)carbonylmethyl-1H-1,4-benzo[f]diazepin-3-yl]ureido}-2-phenylmethyleneaminooxyacetic acid, (RS)-2-{3-{3-[2,3-dihydro-2-oxo-5-phenyl-1-(1-pyrrolidinyl)carbonylmethyl-1H-1,4-benzo[f]diazepin-3-yl]ureido}phenyl}-2-(carboxymethyloxyimino)acetic acid, (RS)-5-{3-{3-[2,3-dihydro-2-oxo-5-phenyl-1-(1-pyrrolidinyl)carbonylmethyl-1H-1,4-benzo[f]diazepin-3-yl]ureido}benzyl}-2,2-dimethyl-1,3-dioxane-4,6-dione, (E)-(RS)-2-{3-{3-[1-(N,N-diethylcarbamoylmethyl)-2,3-dihydro-2-oxo-5-phenyl-1H-1,4-benzo[f]diazepin-3-yl]ureido}phenyl}ethylenesulphonic acid, (RS)-5-{3-{3-[1-(N,N-diethylcarbamoylmethyl)-2,3-dihydro-2-oxo-5-phenyl-1H-1,4-benzo[f]diazepin-3-yl]ureido}benzyl}tetrazole, (E)-(RS)-3-{3-{3-[1-(N,N-diethylcarbamoylmethyl)-2,3-dihydro-2-oxo-5-phenyl-1H-1,4-benzo[f]diazepin-3-yl]ureido}-alpha-hydroxyiminophenylacetic acid, (RS)-{3-{3-[1-(N,N-diethylcarbamoylmethyl)-2,3-dihydro-5-(2-fluorophenyl)-2-oxo-1H-1,4-benzo[f]diazepin-3-yl]ureido}phenylthio}acetic acid, (RS)-{4-{3-[2,3-dihydro-1-(3,3-dimethylpiperidino)carbonylmethyl-2-oxo-5-phenyl-1H-1,4-benzo[f]diazepin-3-yl]ureido}phenylthio}acetic acid, (E)-(RS)-3-{3-[2,3-dihydro-2-oxo-5-phenyl-1-(3,3-dimethylpiperidino)carbonylmethyl-1H-1,4-benzo[f]diazepin-3-yl]ureido}phenyl}-2-propenoic acid, (RS)-{4-{3-[2,3-dihydro-2-oxo-5-phenyl-1-(1-pyrrolidinyl)carbonylmethyl-1H-1,4-benzo[f]diazepin-3-yl]ureido}phenylthio}acetic acid, potassium (RS)-1-{3-[3-(RS)-2,3-dihydro-2-oxo-5-phenyl-1-methyl-1H-1,4-benzo[f]diazepin-3-yl)ureido]phenyl}ethanesulphonate, (+)-{3-{3-[2,3-dihydro-2-oxo-5-phenyl-1-(1-pyrrolidinyl)carbonylmethyl-1H-1,4-benzo[f]diazepin-3-yl]ureido}phenylthio}acetic acid, (−)-{3-{3-[2,3-dihydro-2-oxo-5-phenyl-1-(1-pyrrolidinyl)carbonylmethyl-1H-1,4-benzo[f]diazepin-3-yl]ureido}phenylthio}acetic acid, (RS)-{3-{3-[(RS)-2,3-dihydro-2-oxo-5-phenyl-1-(1-pyrrolidinyl)carbonylmethyl-1H-1,4-benzo[f]diazepin-3-yl]ureido}phenylsulphinyl}acetic acid, (RS)-{3-{3-[2,3-dihydro-2-oxo-5-phenyl-1-(1-pyrrolidinyl)carbonylmethyl-1H-1,4-benzo[f]diazepin-3-yl]ureido}phenylsulphonyl}acetic acid, (RS)-2-{3-{3-[(RS)-2,3-dihydro-2-oxo-5-phenyl-1-(1-pyrrolidinyl)carbonylmethyl-1H-1,4-benzo[f]diazepin-3-yl]ureido}phenylthio}propionic acid and their salts.

5. A pharmaceutical composition for inhibiting CCK or gastrin, which comprises an effective amount of at least one compound of formula (I) as claimed in claim 1 in combination with a pharmaceutically acceptable carrier.

6. A method for inhibiting CCK or gastrin which comprises administering to a host in need of said inhibition an effective amount of a compound of formula (I) as claimed in claim 1.

* * * * *